United States Patent
Branch et al.

(10) Patent No.: US 10,506,951 B2
(45) Date of Patent: Dec. 17, 2019

(54) JOINT PLAY QUANTIFICATION AND ANALYSIS

(71) Applicant: ERMI, Inc., Atlanta, GA (US)

(72) Inventors: Thomas P. Branch, Atlanta, GA (US); Shaun K. Stinton, Chamblee, GA (US); Edward Dittmar, Marietta, GA (US); Nathaniel K. deJarnette, Lilburn, GA (US); T. Christopher Madden, Atlanta, GA (US)

(73) Assignee: RoboDiagnostics LLC, Atlanta, GA (US)

(*) Notice: Subject to any disclaimer, the term of this patent is extended or adjusted under 35 U.S.C. 154(b) by 339 days.

(21) Appl. No.: 15/173,157

(22) Filed: Jun. 3, 2016

(65) Prior Publication Data

US 2017/0347924 A1    Dec. 7, 2017

(51) Int. Cl.
*A61B 5/11* (2006.01)
*A61B 5/00* (2006.01)
(Continued)

(52) U.S. Cl.
CPC .......... *A61B 5/1121* (2013.01); *A61B 5/1036* (2013.01); *A61B 5/1127* (2013.01);
(Continued)

(58) Field of Classification Search
CPC ... A61B 5/1121; A61B 5/4528; A61B 5/4533; A61B 5/4585; A61H 1/024
See application file for complete search history.

(56) References Cited

U.S. PATENT DOCUMENTS

| | | | |
|---|---|---|---|
| 4,969,471 | A | 11/1990 | Daniel et al. |
| 5,935,086 | A | 8/1999 | Beacon et al. |

(Continued)

FOREIGN PATENT DOCUMENTS

| | | |
|---|---|---|
| WO | 2014076147 A2 | 5/2014 |
| WO | 2015121830 A1 | 8/2015 |

OTHER PUBLICATIONS

Pugh et al., "Current Concepts in Instrumented Knee-Laxity Testing", Am J Sports Med, 2009, vol. 37, No. 1, pp. 199-210 (Year: 2009).*

(Continued)

*Primary Examiner* — Devin B Henson
(74) *Attorney, Agent, or Firm* — Lempia Summerfield Katz LLC

(57) ABSTRACT

A method includes obtaining rotational data and translational data for a joint, the rotational and translational data being indicative of rotational and translational movement of the joint during rotational and translational joint testing, respectively, the rotational and translational joint testing being implemented by a robotic testing apparatus applied to the joint. A quantity indicative of joint play of the joint is computed. The quantity is computed via a function of the rotational data and the translational data. The method includes determining whether the computed quantity exceeds a joint play threshold and, if the computed quantity exceeds the joint play threshold, comparing the rotational data and the translational data with preset rotational data and preset translational data for the rotational and translation joint testing, respectively.

21 Claims, 11 Drawing Sheets

(51) Int. Cl.
  *A61B 90/00*  (2016.01)
  *A61B 5/103*  (2006.01)
  *A61H 1/02*  (2006.01)

(52) U.S. Cl.
  CPC .......... *A61B 5/4528* (2013.01); *A61B 5/4585* (2013.01); *A61B 90/06* (2016.02); *A61B 5/4533* (2013.01); *A61B 5/702* (2013.01); *A61B 2090/067* (2016.02); *A61H 1/024* (2013.01)

(56) References Cited

U.S. PATENT DOCUMENTS

| | | | |
|---|---|---|---|
| 6,162,189 | A | 12/2000 | Girone et al. |
| 6,324,296 | B1 | 11/2001 | McSheery et al. |
| 7,291,119 | B1 | 11/2007 | de Guise et al. |
| 7,607,440 | B2 | 10/2009 | Coste-Maniere et al. |
| 8,170,716 | B2 | 5/2012 | Coste-Maniere et al. |
| 8,491,574 | B2 | 7/2013 | Blumenkranz |
| 8,571,710 | B2 | 10/2013 | Coste-Maniere et al. |
| 8,888,718 | B2 | 11/2014 | Siston et al. |
| 2003/0109780 | A1 | 6/2003 | Coste-Maniere et al. |
| 2005/0119661 | A1 | 6/2005 | Hodgson et al. |
| 2005/0234332 | A1 | 10/2005 | Murphy |
| 2006/0161051 | A1 | 7/2006 | Terrill-Grisoni et al. |
| 2007/0055176 | A1 | 3/2007 | Branch et al. |
| 2009/0124936 | A1 | 5/2009 | Branch et al. |
| 2010/0010506 | A1 | 1/2010 | Murphy |
| 2012/0046540 | A1 | 2/2012 | Branch et al. |
| 2013/0041289 | A1 | 2/2013 | Sena et al. |
| 2013/0282024 | A1 | 10/2013 | Blumenkranz |
| 2013/0307955 | A1 | 11/2013 | Deitz et al. |
| 2014/0081181 | A1 | 3/2014 | Branch et al. |
| 2014/0135985 | A1 | 5/2014 | Coste-Maniere et al. |
| 2014/0222157 | A1 | 8/2014 | Al Hares et al. |
| 2014/0316242 | A1 | 10/2014 | Musahl et al. |
| 2015/0201867 | A1 | 7/2015 | Peindl et al. |

OTHER PUBLICATIONS

Branch et al., "Rotational laxity greater in patients with contralateral anterior cruciate ligament injury than healthy volunteers", Knee Surg Sports Traumatol Arthrosc, Dec. 18, 2009, vol. 18, pp. 1379-1384, Springer.

Branch et al., "The combination of tibial anterior translation and axial rotation into a single biomechanical factor mproves the prediction of patient satisfaction over each factor alone in patients with ACL reconstructed knees", Knee Surg Sports Traumatol Arthrosc, Sep. 13, 2016, 10 pages, Springer.

Daniel DM, Malcom LL, Losse G, Stone ML, Sachs R, Burks R (1985) Instrumented measurement of anterior laxity of the knee. J Bone Joint Surg Am 67:720-6.

Siebold et al., "Anatomical "C"-shaped double-bundle versus single-bundle anterior cruciate ligament reconstruction in pre-adolescent children with open growth plates", Knee Surg Sports Traumatol Arthrosc, Dec. 16, 2015, vol. 24, pp. 796-806, Springer.

\* cited by examiner

JOINT PLAY QUANTIFICATION AND ANALYSIS

CROSS-REFERENCES TO RELATED APPLICATIONS

This application is related to the concurrently filed and commonly assigned applications entitled "Robotic Joint Testing Apparatus and Coordinate Systems for Joint Evaluation and Testing" (Ser. No. 15/173,510), "Analysis System and Method for Determining Joint Equilibrium Position" (Ser. No. 15/173,520), "Biomechanical Characterization and Analysis of Joints" (Ser. No. 15/173,199), and "Robotic Knee Testing Apparatus and Patient and Apparatus Set-Up Methods" (Ser. No. 15/173,536), the entire disclosures of which are hereby expressly incorporated by reference.

BACKGROUND OF THE DISCLOSURE

Field of the Disclosure

The disclosure relates generally to robotic joint testing.

Brief Description of Related Technology

The knee joint is composed of the femur or thigh bone, the tibia or shin bone, and the patella or knee cap. The bones are connected by fibrous structures called ligaments, which allow a certain amount of "play" or unimpeded motion to exist between the bone structures. Unimpeded motion in a joint can be referred to as "joint play". When joint play is increased or decreased, an abnormal or pathological condition exists in the knee. Attempts have been made in the past to quantify this increase or decrease in joint play of the knee with limited success.

Knee injuries often cause damage to one or more of the structures that form the knee joint. Such injuries typically cause an increase in joint play, or the quantity of motion between the two bones of the knee. Clinicians and patients may characterize the quality of a knee as being 'looser' or of increased laxity; however, laxity does not necessarily imply a change in joint play. A patient may have the sensation of the knee slipping "out of joint" due to an increase in joint play. In other words, this sensation may be described by the patient as the feeling of joint instability. The knee as a system can become unstable such that the tibia is out of normal contact range with the femur. Knee instability may be related in part to an increase in the length of the ligaments that connect the bones together (e.g., damage to the ligament due to a partial or full tear of the ligament), an increase or change in compliance (elastic resilience or stretchiness) of the ligaments, changes in the bone structure of the joint, or any combination thereof. Knee instability may also be related in part to the shape and size of the joint bones. The degree or likelihood of the knee joint bones actually coming out of joint or becoming unstable is related to the amount of stretch or increased length of each knee ligament, the number of knee ligaments involved, and the existence of damage to one or more other support structures of the knee joint, such as the joint bones themselves, the menisci, or the like. Accurate measurement of an increase in ligament length can be critical to restoring a patient's injured or damaged knee to as close as possible to its original functional and anatomical structure and condition.

Knee injuries and ligament damage have been diagnosed using manual tests. These tests are performed by doctors or other medical personnel, i.e., clinicians, on the patient in order to detect and measure changes to joint play in order to diagnose damage to the knee ligaments or other knee joint support structures. There are a number of commonly known manual tests used to evaluate increased joint play associated with ligament injuries in the knee. The three most common tests, by their commonly used names, include the Dial test, the Lachman test, and the Varus-Valgus test. Because these tests are performed manually by individual medical personnel, these tests naturally are limited by the specific clinician's subjective evaluation. The subjective nature of the tests may hinder the precision or accuracy of any diagnosis of the extent of ligament lengthening (or damage), the change in ligament compliance or elastic resilience, i.e., stretchiness, changes in the bone structure, or combinations thereof.

The Lachman's test, or anterior-posterior drawer test at 30 degrees, is performed with a patient lying in a supine position. The clinician will bend the patient's knee joint at approximately 20 to 30 degrees. The clinician places one hand on the patient's upper thigh and their other hand below the upper part of the patient's calf. The clinician then applies upward and downward pressure under the patient's calf while opposing that force with downward and upward pressure on the patient's thigh. This induces an anterior and posterior translation between the patient's femur and tibia. The degree of translation is subjectively determined by the clinician to diagnose the injury or joint damage. In addition to the anterior and posterior motion, the clinician feels other off-primary axis motions occurring in the knee when applying the primary axis anterior-posterior load. Off-axis motions are those motions not oriented directly along the pathway of motion caused by the torque or other actuation directed to the limb. In other words, if the actuation is directed along the Y-axis in a positive and negative direction, off-axis motion would be oriented along translations along the X-axis or Z-axis, or along the rotations around all three axes.

The Dial test, or the 30 degree Tibial Axial Rotation test, is performed with the patient lying in the supine position with the knee at 30 degrees and the heel on the table. The foot is rotated in maximum internal rotation followed by maximum external rotation. The amount of rotation occurring both at the proximal tibia and at the foot is noted.

The Varus-Valgus Stress test can be performed under many conditions, the most common one having the patient supine and the lower leg cradled in the clinician's arms. Pressure is applied in abduction and adduction with movement at the foot while a hand stabilizes the femur. An assessment of both motion and separation of the joint space is noted along its medial and lateral joint line.

A fourth test combines all of the previous tests into a complex maneuver called the Pivot Shift test. The Pivot Shift test is similarly performed with the patient lying in a supine position. The leg is straightened out so that the knee joint is placed in full extension (x-axis rotation). A valgus or side-to-side outward rotation (y-axis rotation) force and an internal or twisting rotation (z-axis rotation) force is applied to the knee to allow the lateral tibia to slip anteriorly from underneath the lateral femoral condyle. As the knee is flexed or bent (x-rotation), the tibia is allowed to slip suddenly back underneath the femoral condyle. The clinician subjectively determines whether there is an abnormal external rotation (z-axis rotation) and posterior translation (y-axis translation) of the tibia with respect to the femur. The degree of shift that is felt or determined by the clinician represents to the clinician the relative increased translation (y-axis translation) of the lateral side of the knee with respect to the increased translation (y-axis translation) of the medial side of the knee. A sudden shift in the knee joint is felt by the clinician and represents the point at which the tibia bone slides from in front of the radius of curvature of the curved end of the femur back to its normal position under the femoral condyle. The Pivot Shift test is inherently subjective, difficult to accurately perform, difficult to teach, and ultimately difficult to quantify.

Grading each test usually involves the opinion of the physician placing the test into three categories, e.g., Grade I, Grade II or Grade III. For the pivot shift test, the grading depends upon the speed and intensity of the knee joint slipping back into place. For other tests, the grading represents the amount of motion detected by the clinician during the examination. For example, Grade I would be 0-5 mm of joint play. Grade II would represent 6-10 mm of joint play. Grade III would represent 11-15 mm of joint play.

For a ligament injury to be diagnosed, one or more of these tests is considered abnormal, suggesting a Grade II or more increase in joint play. In the past the results of a single test was used to diagnose a ligament tear. Often this "one dimensional" diagnosis would result in a surgical procedure. For instance, in order for a clinician to diagnose an injured ACL using the aforementioned manual tests, the clinician determines whether the knee feels abnormal. The accuracy of an ACL injury diagnosis provided by a clinician using currently known manual tests depends on the skill and experience of the clinician and their subjective determinations. A misdiagnosis can lead to unnecessary treatment or unnecessary delay in treatment, which may result in an increased risk for further injury or damage to the patient's knee joint.

A combination of these clinical examination tests can be used to diagnose lateral collateral ligament (LCL), medial collateral ligament (MCL), and posterior cruciate ligament (PCL), and other knee ligament injuries. Each manual test relies on grading the degree of length (or damage) increase in the ligament based on relative increase in joint play into three Grades or categories. There is no effort to grade the compliance or elastic resilience, i.e., stretchiness, of the ligaments using these manual tests. An expert clinician may instead describe the ligament in terms of its subjective feel to the clinician, e.g., by stating that the joint has a soft or hard endpoint. Also, a knee joint may have injury or damage to more than one ligament or structure. The more ligaments and structures of the knee joint that are damaged, the more complex it is for the clinician to perform a manual knee examination. This can make the full diagnosis less accurate and less precise.

Clinicians and surgeons manually examine the injured knee joint for altered or increased joint play. However, due to the variability in size of the patient, size and experience of the surgeon, and the potential degree or subtlety of an injury, consistent and reproducible reports of joint play between surgeons is not possible. Many reports have documented that, whether diagnosis is performed manually or even with manual arthrometers, the manual application of torque to the knee joint varies widely between clinicians. This results in inconsistencies in the examination of joint play and, ultimately, the diagnosis made by the clinician.

Others have attempted to reduce the manual nature of such joint testing by applying an instrument to the knee joint during testing. The objective has been to mechanically or objectively quantify or measure a change in the structure of the knee after ligament damage. Several devices have been developed in attempting to more accurately quantify the extent of injury or relative displacement and compliance of a ligament in the knee. In one example, such devices have been developed by Medmetric Corp. These devices include the KT-1000 and KT-2000 models. The KT devices are intended to measure the anterior-posterior translation of the tibia with respect to the femur. The KT devices attach to the patient's tibia during testing.

The KT devices attempt to quantify the findings achieved by a clinician performing the Anterior-Posterior Drawer test at 30 degrees (Lachman's test) and the Anterior-Posterior Drawer test at 90 degrees. Force is applied to a handle on the device, which measures the force and delivers the amount of applied force to the clinician, which is indicated through sounds, such as a low pitched sound for a 15 pound force and a higher pitched sound for a 20 pound force. The applied force in the KT devices pulls anteriorly along the y-axis through a strap that wraps underneath the patient's calf. The translation is determined using a technique that measures the relative motion between a pad placed against the anterior tibia and a pad placed against the patella. The KT devices do not measure relative displacement or compliance in any of the other degrees of freedom in the knee. Also, quantified results from using the KT-1000 or KT-2000 devices have been found to not correlate with patient satisfaction.

Laxity testing in the past, both manual and instrumented, has been found to be inconsistent, both when testing the same patient from day to day and when two different examiners test the same patient. This is in part due to 1) the subjective nature, among examiners and among patients, of these prior examination and diagnosis techniques, 2) the complexity of the anatomy of the knee, 3) the lack of a system or method that is reliably repeatable to measure knee laxity, and 4) the accumulation of error introduced at different stages of an examination or diagnosis. Introducing significant error at any one or more steps during a test can greatly affect, and invariably reduce, the accuracy of the ultimate diagnosis. The degree of error may often overwhelm the ability to obtain an accurate diagnosis.

SUMMARY OF THE DISCLOSURE

In accordance with one aspect of the disclosure, a method includes obtaining rotational data and translational data for a joint, the rotational and translational data being indicative of rotational and translational movement of the joint during rotational and translational joint testing, respectively, the rotational and translational joint testing being implemented by a robotic testing apparatus applied to the joint, computing a quantity indicative of joint play of the joint, the quantity being computed via a function of the rotational data and the translational data, determining whether the computed quantity exceeds a joint play threshold, and, if the computed quantity exceeds the joint play threshold, comparing the rotational data and the translational data with preset rotational data and preset translational data for the rotational and translation joint testing, respectively.

In accordance with another aspect of the disclosure, a system includes a memory in which input instructions, quantification instructions, and analysis instructions are stored, and a processor coupled to the memory and configured through execution of the input instructions to obtain rotational data and translational data for a joint, the rotational and translational data being indicative of ranges of rotational and translational motion of the joint during rotational and translational joint testing, respectively, the rotational and translational joint testing being implemented by a robotic testing apparatus applied to the joint. The processor is configured through execution of the quantification instructions to compute a quantity synthetically indicative of joint play of the joint via synthesis of the rotational data and the translational data. The processor is configured through execution of the analysis instructions to determine whether the computed quantity exceeds a joint play threshold. The processor is configured through execution of the analysis instructions to compare the rotational data and the translational data with rotational and translational thresholds, respectively, if the computed quantity exceeds the joint play threshold.

In accordance with yet another aspect of the disclosure, a system includes a robot testing apparatus configured to implement rotational joint testing and translational joint testing of a joint and further configured to detect a range of rotational motion and a range of translational motion for the joint, a memory in which input instructions, quantification instructions, and analysis instructions are stored, and a processor in communication with the robot testing apparatus and coupled to the memory. The processor is configured through execution of the input instructions to obtain, via the robot testing apparatus, rotational data indicative of the range of rotational motion and translational data indicative of the range of translational motion. The processor is configured through execution of the quantification instructions to compute a quantity indicative of joint play of the joint, the quantity being computed via a function of the rotational data and the translational data. The processor is configured through execution of the analysis instructions to determine whether the computed quantity exceeds a joint play threshold. The processor is further configured through execution of the analysis instructions to compare the rotational data and the translational data with rotational and translational thresholds, respectively, if the computed quantity exceeds the joint play threshold.

BRIEF DESCRIPTION OF THE DRAWING FIGURES

For a more complete understanding of the disclosure, reference is made to the following detailed description and accompanying drawing figures, in which like reference numerals may be used to identify like elements in the figures.

Figure 1:
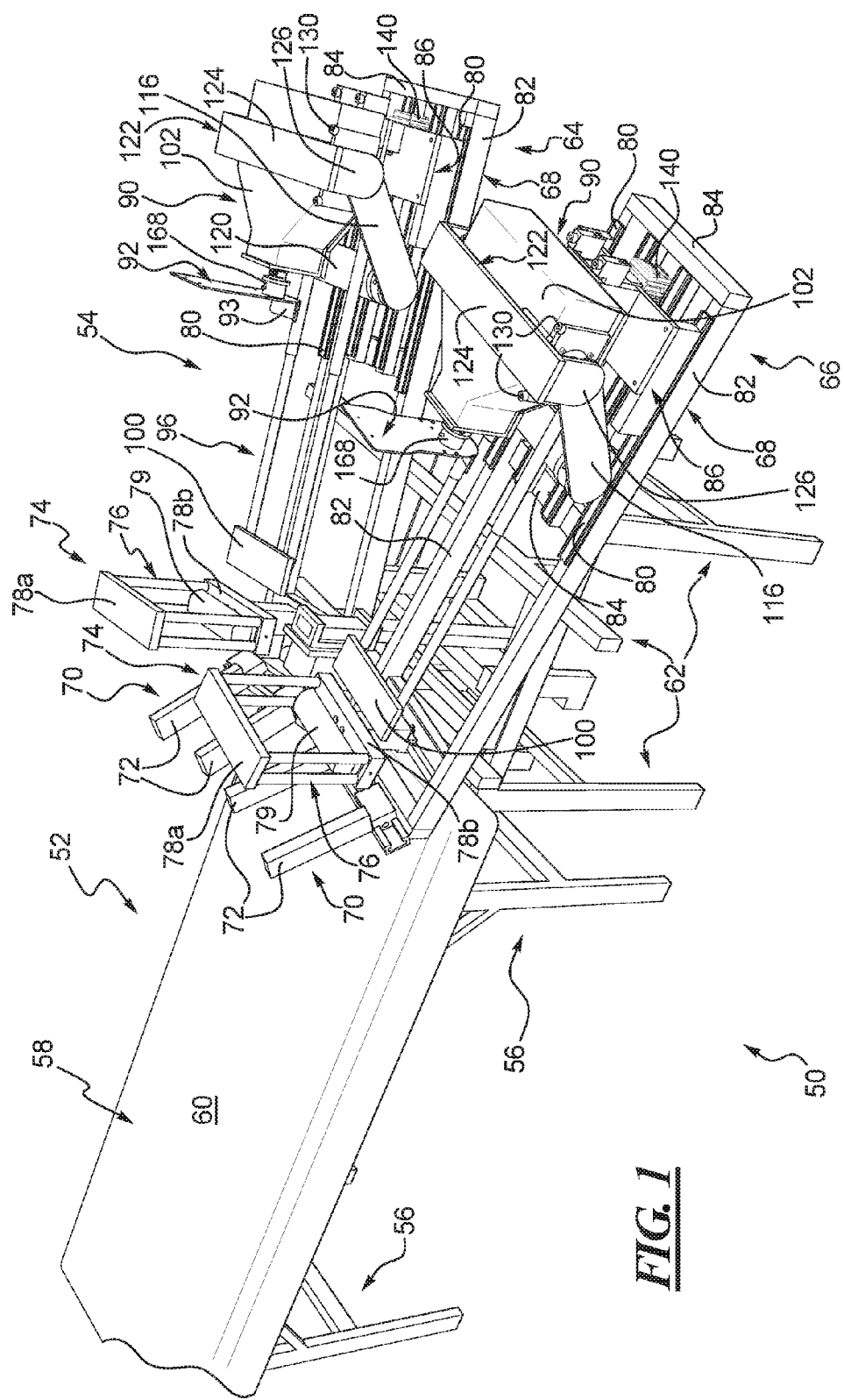
FIG. 1 shows a perspective view of one example of a robotic knee testing (RKT) apparatus according to the teachings of the present disclosure.

The disclosed methods, systems, and devices may assume various forms. Specific examples are illustrated in the drawing (and are hereafter described) with the understanding that the disclosure is intended to be illustrative, and is not intended to limit the invention to the specific examples described and illustrated herein.

DETAILED DESCRIPTION OF THE DISCLOSURE

Systems and methods involving quantification of joint play are described. A quantity indicative of joint play is computed as a function of, or via combination or synthesis of, various different movements of the joint. The joint play quantity may be referred to as joint play area or joint play volume. The movements may correspond with one or more rotational movements and one or more translational movements. In the context of a knee, the translational movement may occur during an anterior-posterior test, while the rotational movement may occur during an external-internal rotation test and/or a varus-valgus test.

The combination or synthesis of the data resulting from different tests into a single measure or factor may result in an artificial or synthetic quantity. For instance, the units of the underlying data may not lend themselves to combination. In some rotational and translational cases, for example, the combination of the data results in a quantity having the units of distance-degrees. However, despite the artificial or synthetic nature of the quantity, the quantity is nonetheless useful in assessing the condition and/or other characteristics of a joint.

Synthesizing or combining data from multiple, different tests helps to avoid undue reliance on a single test for joint assessment. For instance, the synthesis or combination avoids disagreements among surgeons as to whether an assessment of anterior-posterior laxity or the rotational laxity is the most important factor in determining patient satisfaction and function after a knee injury. The synthesis or combination also avoids reliance on the pivot shift test, a subjective test which is difficult for surgeons to perform consistently.

The joint play quantity provides a single factor to be used for comparisons or other analysis directed to whether surgery is warranted or the joint is otherwise abnormal. The quantification may thus support a unilateral assessment of joint condition and/or other characteristics. For example, the quantity may be compared with a joint play threshold.

The comparison or other unilateral assessment involving the joint play quantity may be used to determine whether further analysis is warranted. For example, a determination that the quantity exceeds the threshold may thus serve as a prerequisite to further analysis and/or a determination of a particular abnormality. Exceeding the joint play threshold may thus be indicative of a joint abnormality in general. The further analysis may be used to provide more specificity regarding the abnormality.

In some cases, the further analysis includes or involves comparing the results of the individual or constituent tests underlying the computation or synthesis of the joint play quantity. For instance, the rotational and translational data for the joint may be indicative of ranges of motion achieved during the respective constituent tests. Those respective ranges of motion may then be compared to thresholds for those movements. In some cases, a profile for the joint is compiled indicative of those constituent comparisons. The profile may then be analyzed or assessed to identify an abnormality of the joint.

Although described in connection with a number of examples involving knee testing and evaluation, the disclosed systems and methods are not limited to a particular type of joint. The systems and methods are also not limited to particular types of tests. The nature of the tests may vary considerably in conjunction with the type of joint being assessed or evaluated. The data from any number of tests may be combined or synthesized.

Although described in connection with a number of examples of a robotic testing apparatus, the source of the data obtained by the disclosed systems and methods may vary. A variety of different test devices and equipment may be used in conjunction with, and/or as part of, the disclosed systems and methods. As described below, the nature of the data acquired by the test equipment may vary as well.

Turning now to the drawings, FIG. 1 shows a robotic testing apparatus 50 in accordance with one example. In this case, the robotic testing apparatus 50 is an RKT apparatus. Details regarding examples of the RKT apparatus 50 are described in U.S. Patent Publications Nos. 2014/0081181 and 2012/0046540, the entire disclosures of which are hereby incorporated herein by reference.

The RKT apparatus 50 of FIG. 1 generally has a patient support or, as identified herein, a table assembly 52. The RKT apparatus 50 also has a robotic mechanism or limb manipulation device, identified for ease of description herein as a robot 54, positioned at one end or edge of the table assembly. The table assembly 52 in this example has a supporting frame that is identified herein as a base 56 beneath a patient platform 58. The base 56 is configured to rest on a floor or surface and to support the patient platform 58 above the floor. The patient platform 58 can include a substantially rigid or sturdy panel (not shown) capable of holding and supporting a patient thereon. The panel can be affixed to or otherwise supported by the base 56. The panel of the patient platform 58 can underlie a padded surface 60, which can include a textile or fabric material that covers a cushion, padding, or the like (also not shown).

As will be evident to those having ordinary skill in the art, the configuration and construction of the table assembly 52 can vary considerably from the example disclosed, illustrated, and briefly described herein. The base 56 and/or the patient platform 58 can each be altered in size, shape, orientation, height, construction, materials, and the like. The base can include multiple legs and frame elements that are assembled or connected to one another, as in the illustrated example. Alternatively, the base can be formed as one unitary support element. The patient platform can also be formed of multiple components and can be fastened to or otherwise attached to the base. Alternatively, the patient platform can an integral, one piece fabricated structure and can be fabricated as part of the base or attached thereto. The table assembly need not be a table, but instead can be a chair, a suspension system, or other suitable patient support that is capable of properly positioning and retaining a patient relative to the robot 54 for testing and examination. The table assembly 52 can further include additional features, though not disclosed or described herein, that may be used to assist in positioning a patient on the platform, to assist in maintaining a patient's position on the platform, or to otherwise enhance patient comfort or improve performance of the table assembly, the RKT apparatus, or both.

With reference to FIG. 1, the robot 54 in this example can include a main or primary support frame structure, identified herein for ease of description as a frame 62. The frame 62 may optionally be coupled to, a part of, or otherwise supported by or connected to a portion of the base 56 of the table assembly 52, as shown in FIG. 1. Alternatively, the frame of the robot 54 can be an extension of, connected to, or otherwise supported by a portion of the patient platform 58. In a further alternative, the frame can be some combination of such supporting structures and arrangements or can be a completely separate structure. In any case, the frame 62 in this example supports and positions the robot 54 of the RKT apparatus 50 at one end of the table assembly 52.

Figure 2:
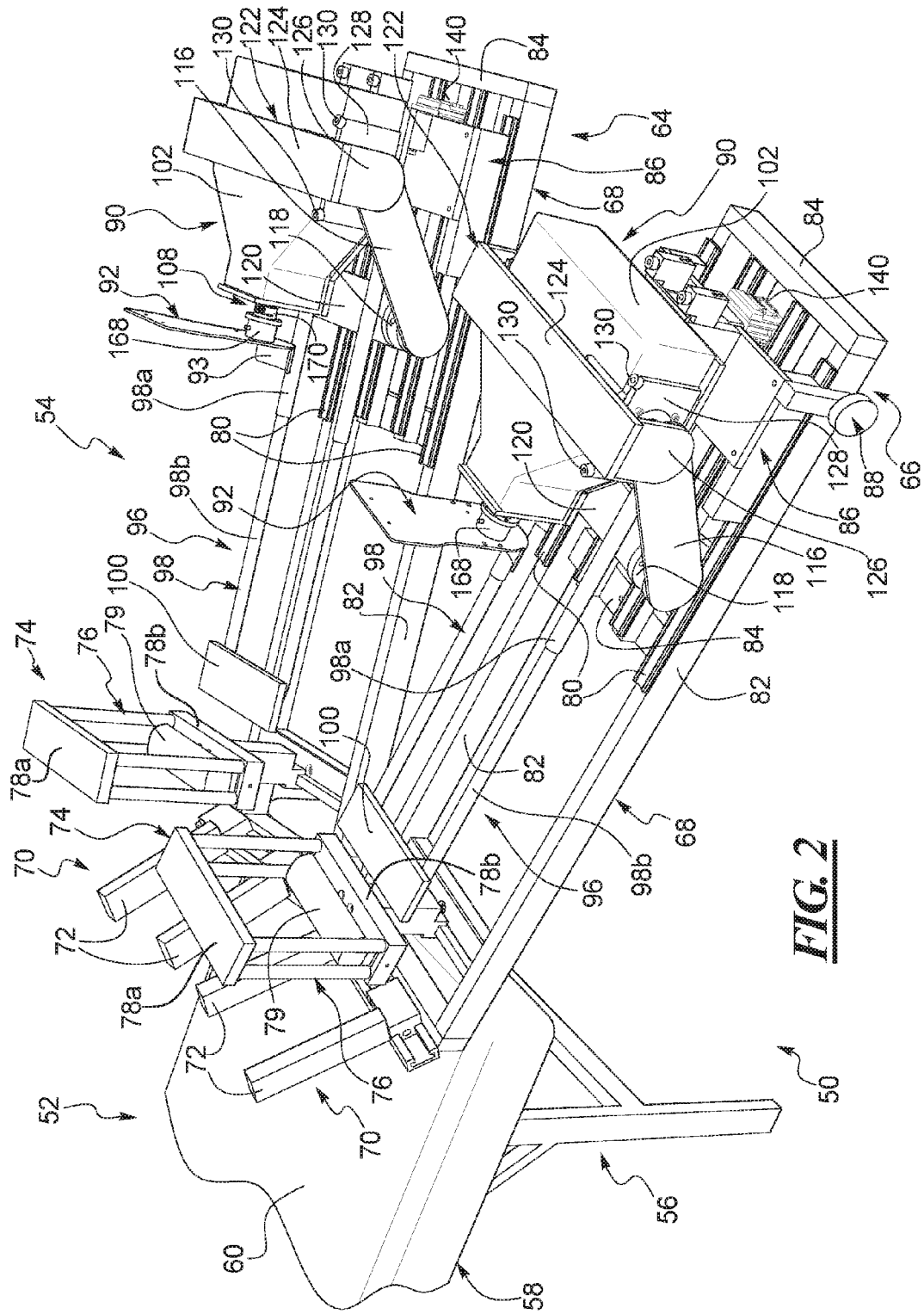
FIG. 2 shows an enlarged view of a limb evaluation device or robot of the RKT apparatus of FIG. 1.
Figure 3:
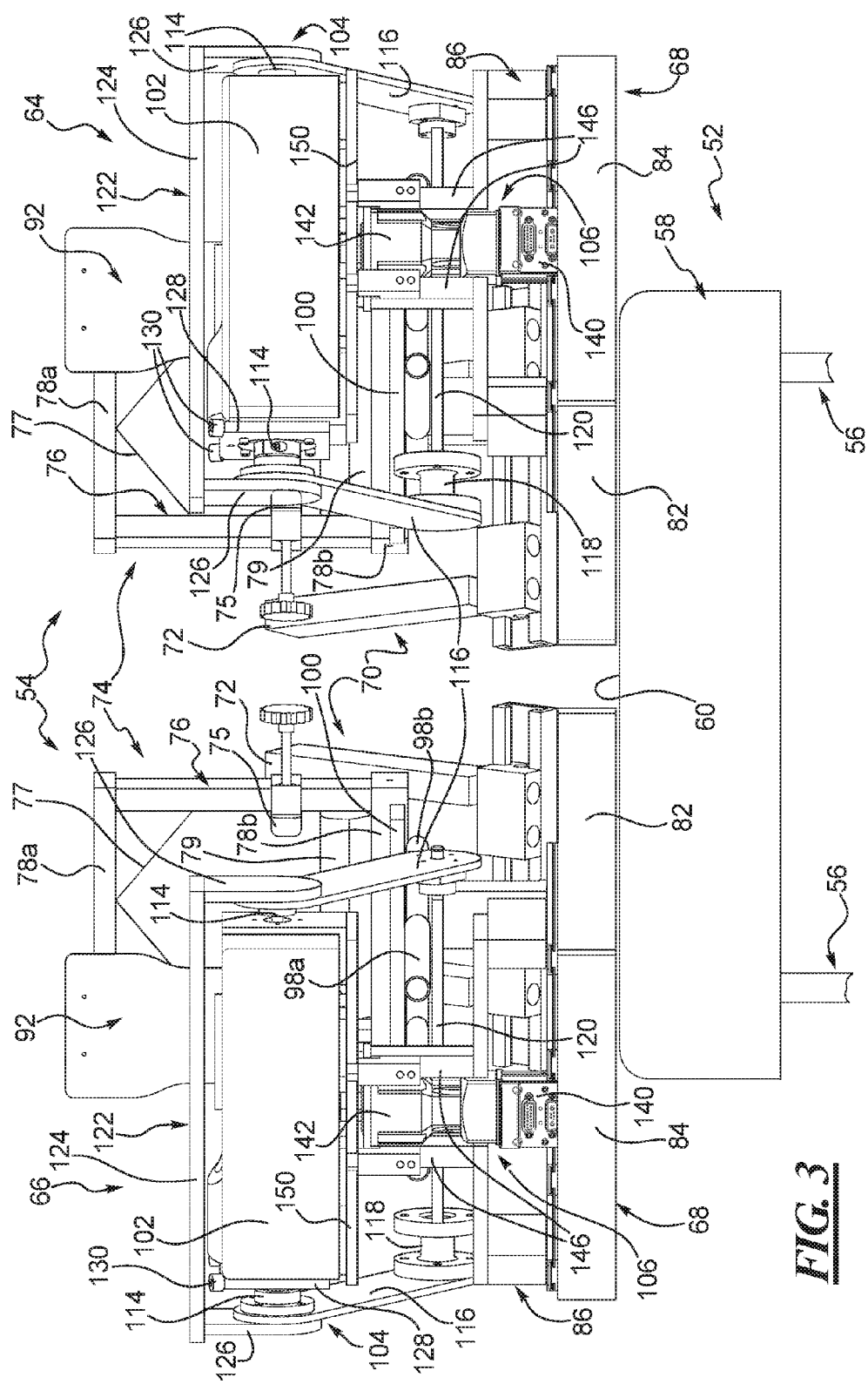
FIG. 3 shows an end view of the robot when viewed from the right hand side in FIG. 2.

In the disclosed example and with reference to FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical, if desired, and each is constructed to support and evaluate a left leg and right leg, respectively, of a patient. Therefore, like reference numerals are used herein to identify common parts of each of the two leg portions 64, 66 that have the same construction. The left and right leg portions 64, 66 each have a sub-frame 68 that, in this example, is supported by the frame 62 of the robot 54. Each sub-frame 68 supports the components and parts of the corresponding left and right leg portions 64, 66. For ease of description, the right leg portion 66 of the robot 54 is described in more detail below with the understanding that the left leg portion 64 has or may have the same overall construction. Differences between the two leg portions are identified herein, if and as needed. It is possible that an RKT apparatus is provided that has only one leg portion for evaluating only one leg of a patient at a time. However, in the disclosed example, the RKT apparatus 50 has left and right leg portions 64, 66.

Figure 4:
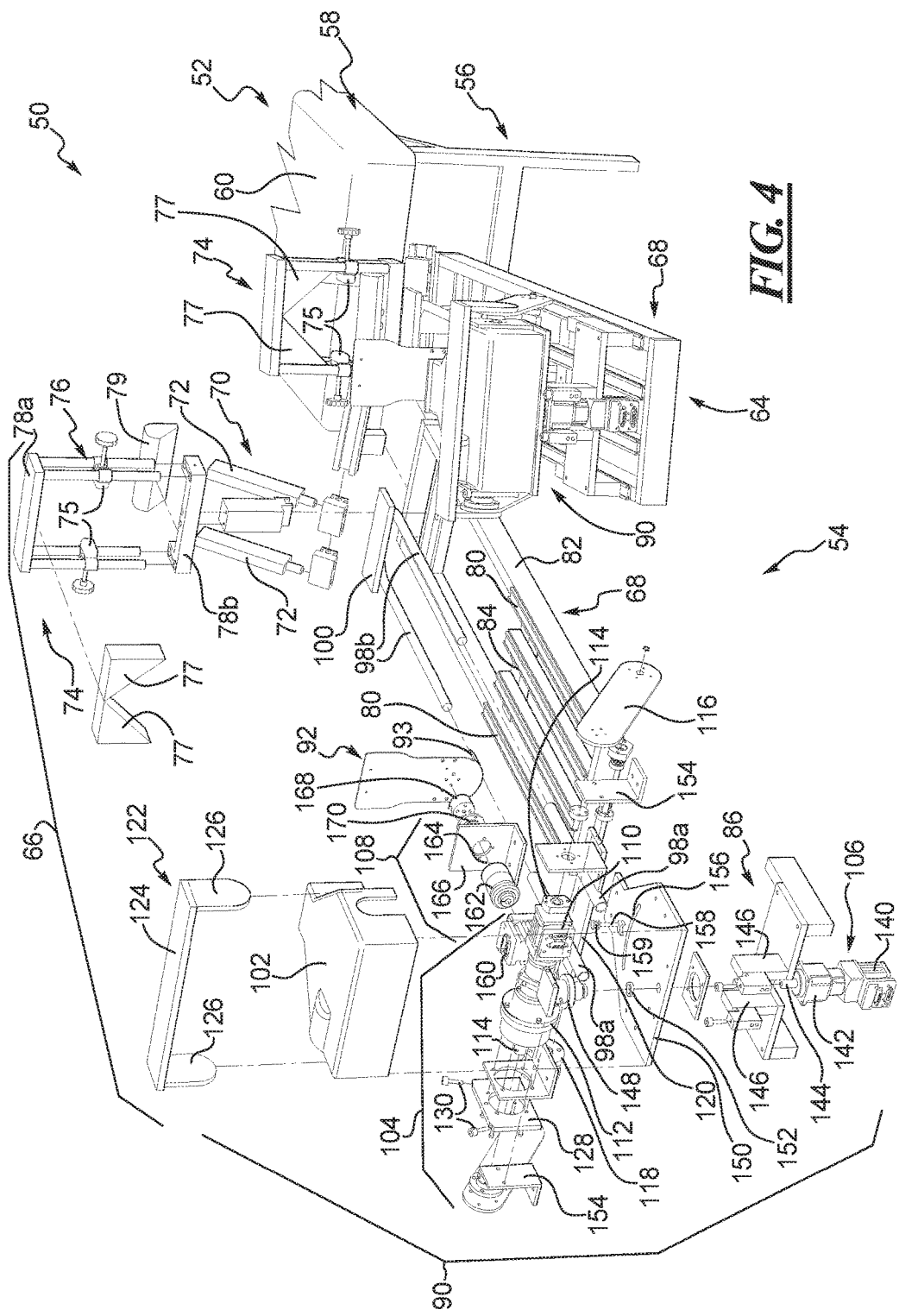
FIG. 4 shows a partial exploded view of the robot of FIG. 2 with the right leg portion of the robot exploded.
Figure 5:
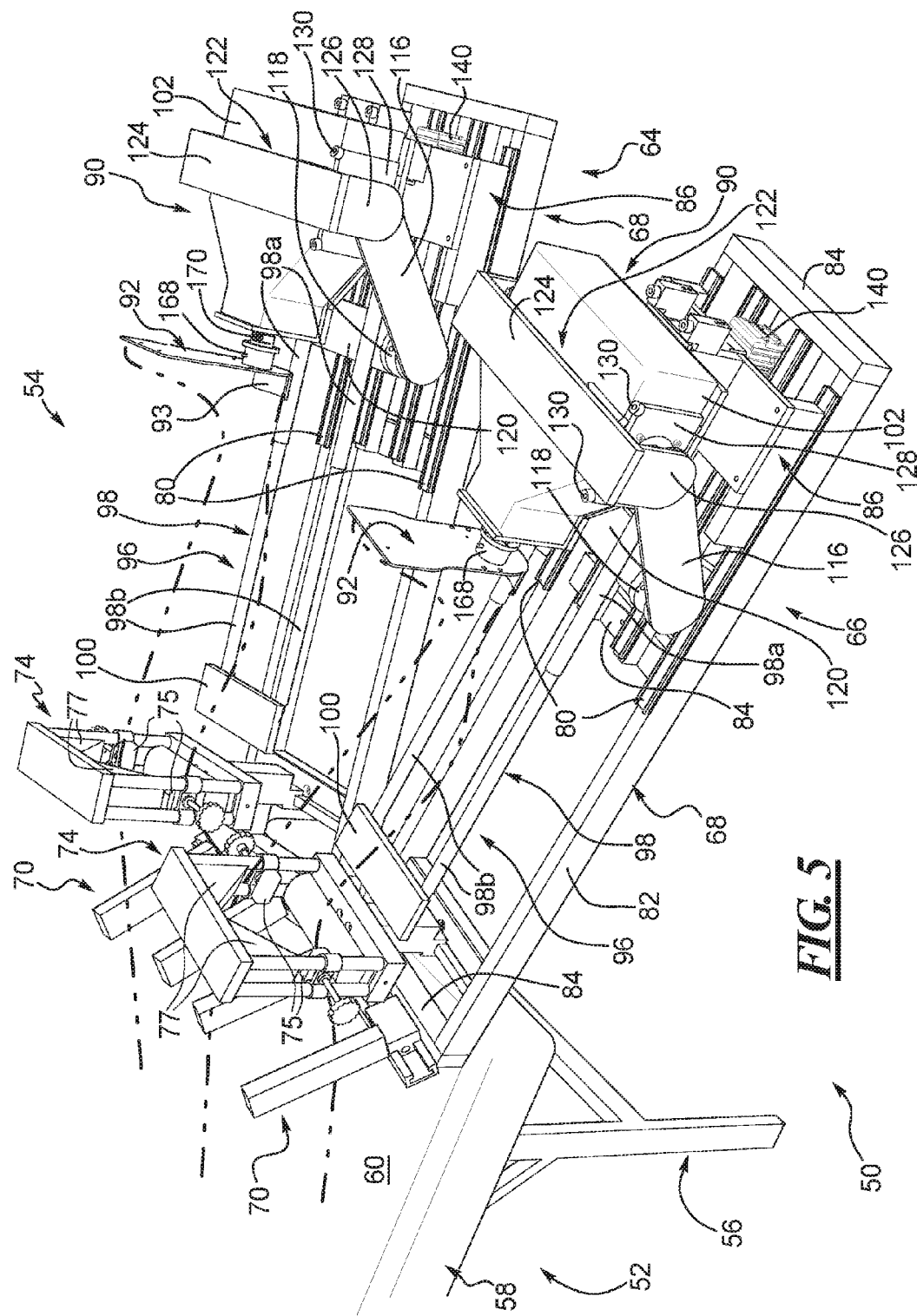
FIG. 5 shows the robot of FIG. 2 and depicts left and right legs of a patient positioned relative to the left and right leg portions of the robot.

As depicted in FIGS. 2-4, the right leg portion 66 has a thigh stabilizer 70 positioned closest to the table assembly 52. The thigh stabilizer 70 can be mounted to the frame 62 or the sub-frame 68, or can be otherwise mounted to a portion of the RKT apparatus 50 in a manner suitable for use as described below. The thigh stabilizer 70 can be constructed so as to be positionally adjustable to accommodate a wide range of patients of different size. Alternatively, the thigh stabilizer 70 can be mounted in a fixed position relative to the table assembly 52, whereby the position of the patient on the table assembly 52 and relative to the thigh stabilizer 70 might be adjustable. In either embodiment, the thigh stabilizer 70 should be positioned or positionable to contact a portion of a patient's upper leg or thigh above the knee, as depicted in FIG. 5.

The thigh stabilizer 70 in this example has a pair of femur clamping elements 72, i.e., medial and lateral clamping elements, that are laterally spaced apart and width-wise adjustable relative to one another. Though not shown herein, the clamping elements can include a pad or pads on the thigh facing surfaces, if desired, to provide a degree of comfort for a patient. The femur clamping elements 72 can be side-to-side adjusted in order to clamp or otherwise securely hold a patient's right femur and thigh in a substantially fixed side-to-side position during testing, evaluation, or treatment, as described below. If the thigh stabilizer 70 is positionally adjustable, it should be capable of being secured in a fixed selected position, once properly adjusted for a given patient, relative to the table assembly 52 and/or robot 54 during testing, evaluation, or treatment. The configuration and construction of the thigh stabilizer 70 can vary considerably from the example shown herein. The clamping elements 72 can be replaced by other suitable securing or clamping devices or elements and the mechanisms to adjust and secure the thigh stabilizer 70 can also vary.

The right leg portion 66 also has a knee stabilizer 74 positioned adjacent the thigh stabilizer. The knee stabilizer 74 can also be mounted to the frame 62 or the sub-frame 68, or can be otherwise mounted to a portion of the RKT apparatus 50 in a manner suitable for use as described below. The knee stabilizer 74 can optionally also be constructed so as to be lengthwise or longitudinally positionally adjustable to accommodate a wide range of patients of different size. The knee stabilizer can also be side-to-side adjustable as well. Alternatively, the knee stabilizer 74 can be mounted in a fixed position relative to the table assembly 52, whereby the position of the patient on the table assembly 52 and relative to the knee stabilizer 74 may be adjustable. In either embodiment, the knee stabilizer 74 should be positioned or positionable to contact the knee or patella at the lower end of a patient's femur and thigh, as depicted in FIG. 5.

The knee stabilizer 74 acts as a knee or patellar clamp and can include a framework 76 arranged to surround and clamp onto a patient's joint or knee. The knee stabilizer 74 in this example has a pair of patellar clamping elements, including an upper clamping element 78a and a lower clamping element 78b, that are vertically spaced apart and adjustable relative to one another along the framework 76. The patellar clamping elements 78a, 78b can be vertically adjusted in order to clamp or otherwise securely hold the lower end of a patient's right femur and patella in a substantially fixed vertical position during testing, evaluation, or treatment, as described below. If the knee stabilizer 74 is positionally adjustable, it should be capable of being secured in a fixed selected position, once properly adjusted for a given patient, relative to the table assembly 52 and/or robot 54 during testing. The configuration and construction of the knee stabilizer 74 can vary considerably from the example shown herein. The patellar clamping elements 78a, 78b can be replaced by other suitable securing or clamping devices or elements and the mechanisms to adjust and secure the knee stabilizer 74 can also vary.

Though not shown in all of the figures, the knee stabilizer 74 can include a plurality of substantially rigid and/or resilient pads for holding and restraining the knee and patella of a patient. In one example, the knee stabilizer knee can include a pair of side-to-side opposed Varus-valgus pads 75 that are adjustable, as shown and described below, toward and away from one another across the framework 76. The knee stabilizer 74 can also include one or more upper pads 77 on the upper clamping element 78a and a lower pad 79 on the lower clamping element 78b. The pads 75, 77, and/or 79 can be configured and arranged to lie adjacent the patient's knee. The various pads 75, 77, and 79 can be configured to prevent the framework 76 and the patellar clamping elements 78a, 78b from directly contacting the patient's knee, but also to assist in restraining the knee and inhibiting movement during testing. The pads 75, 77, and/or 79 can be solid, hollow, pressurized, hydraulically filled, pneumatically filled, or the like and can be rubber, foam, or otherwise formed of suitable materials. In one example as shown, the pad or pads 77 on the upper patellar clamping element 78a can be configured to define a V-shape within the framework 76. The patient's leg can then be captured within the V-shape as the upper and lower patellar clamping elements 78a, 78b are drawn toward one another to capture and hold the patient's leg still during a procedure. In particular, the stabilizer 74 and these pads 77 can aid in constraining the patella during testing. The Varus-valgus pads 75 can also be adjusted to restraint movement of the patient's knee in a side-to-side direction during at least Varus-valgus testing, as described below.

The thigh stabilizer 70 and/or the knee stabilizer 74 may be mechanically adjustable to manually fit and accommodate different sized patients. In one alternative, the thigh stabilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh and knee stabilizers 70 and 74. In yet another alternative, the thigh stabilizer 70, the knee stabilizer 74, or both, may include two or more such systems or mechanisms for adjusting the respective clamping elements.

The thigh stabilizer 70 and/or femur clamping elements 72 and the knee stabilizer 74 and/or framework 76 and patellar clamping elements 78a, 78b can be formed of metal, plastic, or other suitable materials. The thigh and knee stabilizers 70 and 74 can vary in shape, configuration and construction, as desired. The thigh and knee stabilizers 70 and 74, in combination, are intended to secure a patient's leg in order to hold the femur and patella in a vertically (knee stabilizer) and laterally (thigh stabilizer) fixed position during a test, evaluation, or treatment cycle. Features and aspects of the disclosed thigh and knee stabilizers 70 and 74 can vary considerably while accomplishing this objective.

In this example as shown in FIGS. 2 and 4, the sub-frame 68 is configured to define or carry one or more slide tracks 80. The track or tracks 80 can be carried on the free end of the sub-frame 68 that is distal or spaced from the table assembly 52. The sub-frame 68 is formed having a plurality of rails 82 that extend lengthwise and having one or more cross-members 84 that extend laterally between the rails. The tracks 80 can be formed as an integrated part of the rails 82 or other sub-frame components or, as in this example, can be separately mounted to or supported by the rails and/or cross-members 84. One or more trucks or carriages, hereinafter a sled assembly 86 is mounted on or supported by the sub-frame 68 and is slidable along the tracks 80. The sled assembly 86 can slide along the tracks 80 to adjust the position of various parts of the RKT apparatus 50, as described further below. The sled assembly 86 can include a locking mechanism 88 (shown only in FIG. 2) to secure the sled assembly in a desired or selected position along the tracks 80. The locking mechanism 88 can vary in construction and position on the apparatus, as long as it can adequately secure the sled assembly at a selected position. Adjustment of portions of the RKT apparatus 50 can be achieved in other ways. In one example, the RKT apparatus can be mounted to a lift that can raise or lower the apparatus, or portions thereof, and that can slide or roll the robotic components relative to the table assembly 52, either eliminating or altering the need for the tracks 80 and rails 82.

As depicted in FIGS. 2-4, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh and knee stabilizers 70 and 74.

In general, the tibia positioning assembly 90 has a foot holder, which in one example can be a foot plate 92, as in this example. The foot plate 92 has a heel stop 93 at the bottom edge of the foot plate that faces upward and has a contact surface 94 that faces toward the thigh and knee stabilizers 70 and 74. The tibia positioning assembly 90 also has a tibia rod device 96 with one or more rods 98 and a calf contacting or loading portion, which in one example can be a calf plate 100 as in this example. The calf plate 100 is disposed at or near a distal end of the tibia rod device 96. The one or more rods 98 can be lengthwise adjustable. In this example as shown in FIGS. 2-4, the tibia rod device 96 has two tibia rods 98, each of which has two telescoping segments including a fixed segment 98a and a slidable segment 98b that permit length adjustment of the rods 98. Though not shown or described in detail herein, the rods 98 may include a locking mechanism of a suitable type, such as holes and set screws, VALCO ball devices, or the like on one or both of the segments 98a, 98b, that can lock the adjusted rods at a selected length. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 can be configured to physically constrain and hold the foot of a patient against the contact surface 94. In one example, though not shown herein, the foot plate 92 can employ one or more straps that secure the patient's heel against the heel stop 93 and the sole of their foot to the foot plate 92. Likewise, the calf plate 100 can be configured to physically constrain the patient's leg to the calf plate, as described below for certain tests, or can merely lie against and under the patient's calf while not being otherwise secured to the leg for other tests.

Figure 6:
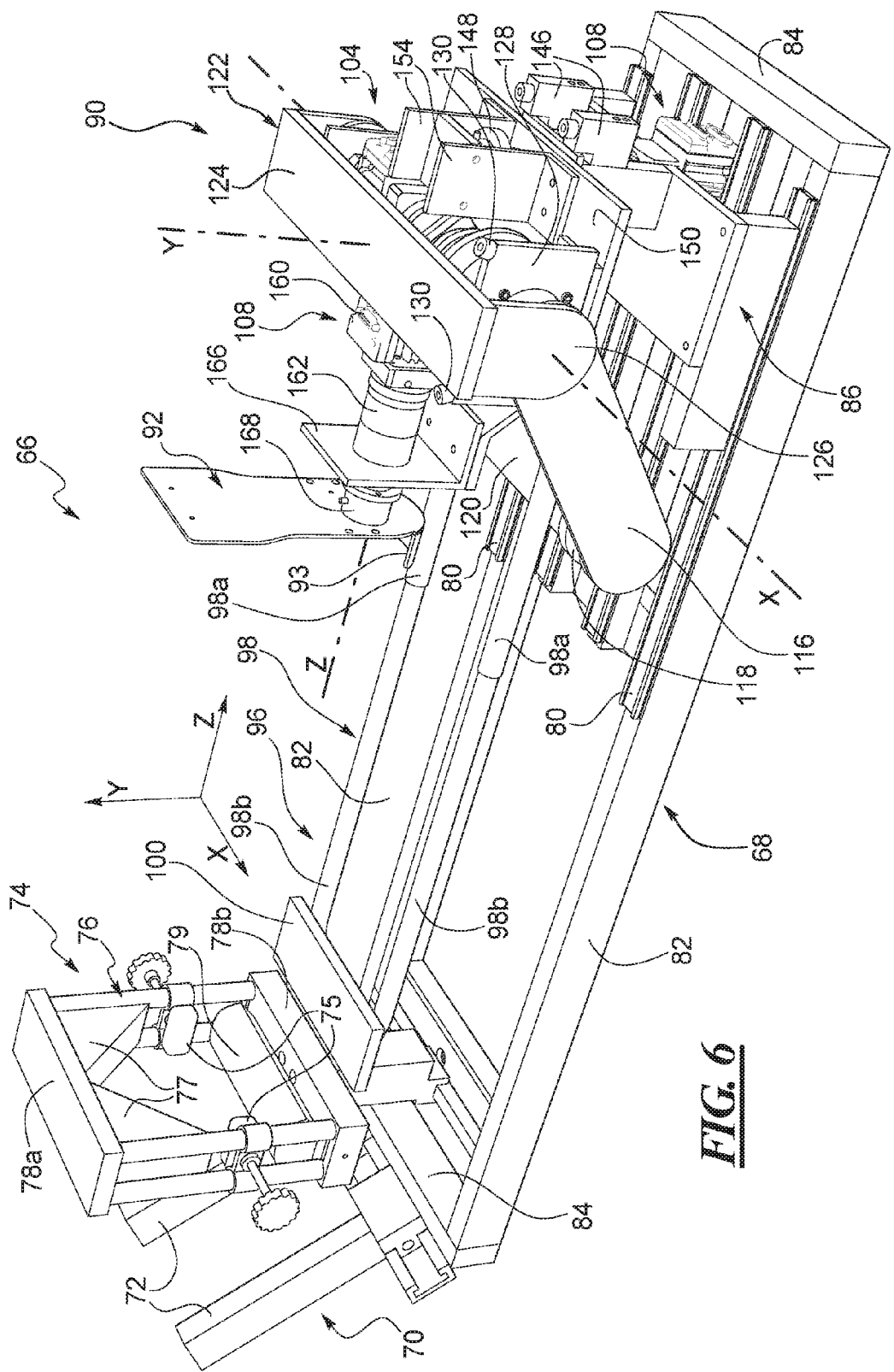
FIG. 6 shows the right leg portion of the robot of FIG. 2 and depicts an X-Y-Z coordinate system defined by the right leg portion.

With reference to FIGS. 4 and 6, the tibia positioning assembly 90 has a drive system with a number of drive components configured to impart specific and controllable movements to the lower leg of a patient. In this example, a substantial number of the drive system components are housed within a shell or housing 102. In other examples, the drive system components may be exposed and the shell eliminated. The drive system in this example generally has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot will also have a similar X-Y-Z coordinate system specific to the left leg portion 64, but independent of the coordinate system for the right leg portion 66.

In other examples, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In other examples, the X-Y-Z axes of the aforementioned coordinate systems may all intersect with one another and may all be orthogonal to one another. In still other examples, none or only two of the axes may intersect and/or none or only two of the axes may be orthogonal to one another.

As shown in FIG. 4, the X-axis drive 104 can include a first motor, such as an electric motor 110, a gearbox 112, and an output shaft 114 that is driven by the motor and gearbox. The opposite ends of the output shaft 114 in this example are fixedly coupled to the upper ends of respective drive links 116 on opposite sides of the housing 102. Thus, as the output shaft 114 is rotated by the motor 110 and gearbox 112, the drive links 116 are also rotated about the X-axis. The drive links 116 in this example are oriented downward and forward from the X-axis. The lower end of one of the drive links 116 is coupled or fixed to an X-axis torque transducer 118. The torque transducer 118 is also coupled or fixed to one end of a cross-plate 120. The lower end of the other drive link 116 is fixed to the opposite end of the drive plate 120. The cross-plate 120 is coupled to and extends laterally across the right leg portion 66 forward of the X-axis between the drive links 116. In this example, the fixed segments 98a of the tibia rods 98 are fixedly mounted to and extend forward toward the knee and thigh stabilizers 70, 74 from the cross-plate 120, as shown in FIGS. 2 and 4.

Figure 7:
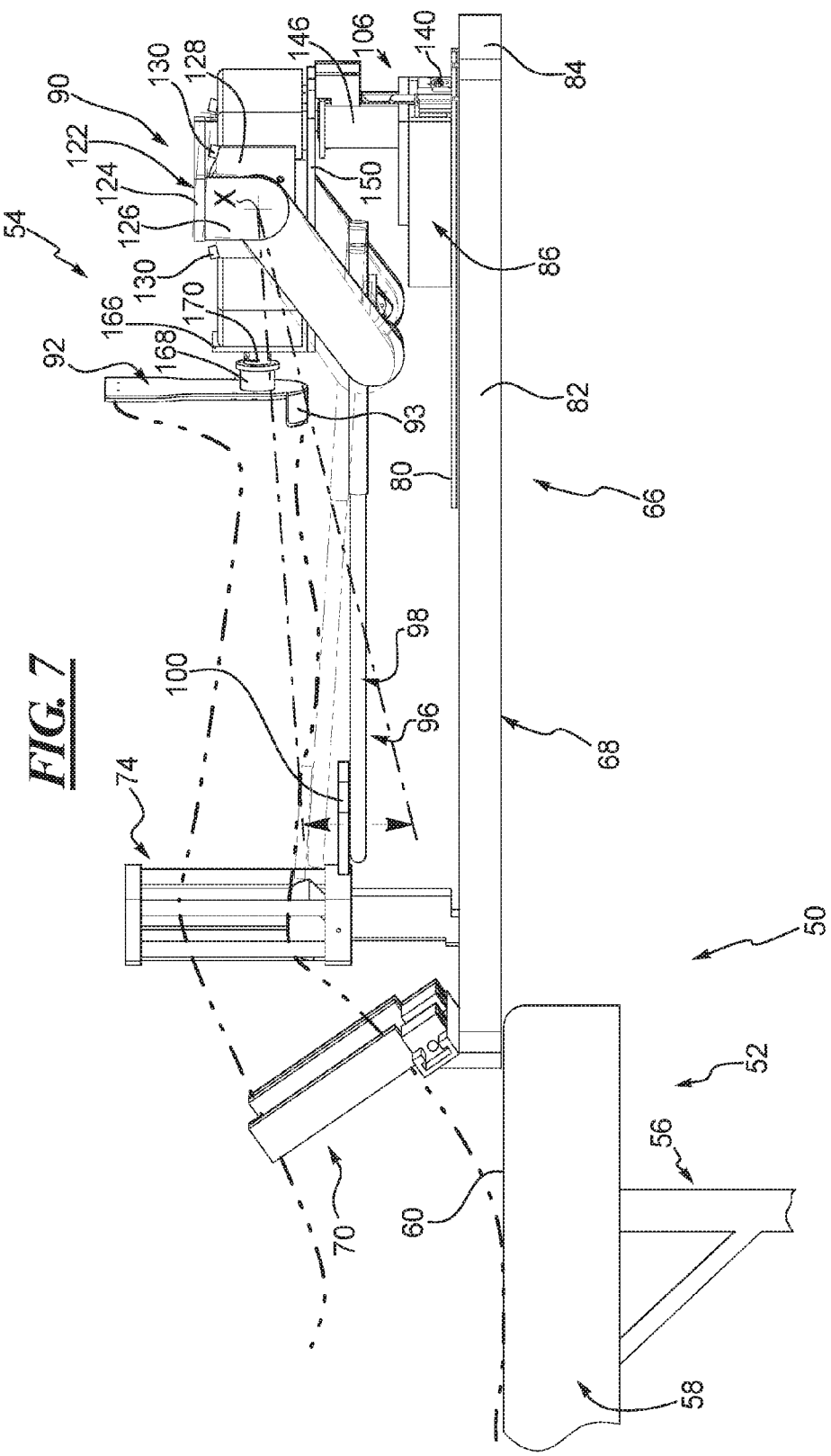
FIG. 7 shows a side view of the robot of FIG. 5 and illustrates anterior-posterior motion of the robot about the X-axis of the right leg portion of the robot.

With reference to FIG. 7, the X-axis drive 104 is configured to conduct an anterior-posterior or A-P test on a patient's knee. Position sensors can be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 7. The motor 110 can reversibly rotate the output shaft 114 through an arc about the X-axis whereby the upper ends of the drive links 116 are rotated through the same arc. This in turn moves, i.e., raises or lowers the lower ends of the drive links 116, which in turn raises or lowers the cross-plate 120 and the fixed segments 98a of the tibia rods 98. Movement of the fixed segments 98a of the tibia rods 98 raises or lowers the slider segments 98b and thus the calf plate 100 carried on the tibia rods 98. The X-axis torque transducer 118 measures the applied torque at the cross-plate 120 caused by the load applied at the calf plate 100 as the calf plate pushes up on the patient's tibia or the tibia rods 98 pull down on the patient's tibia. Motion and load data can be collected by a processor from the sensors relative to the motion in the patient's leg and from the X-axis torque transducer 118 relative to the torque or applied force.

The motor 110 and/or gearbox 112 can be designed to produce a limited range of travel, which may be substantially less than 360 degrees of rotations, in the output shaft 114. In addition or in the alternative, the X-axis drive 104 can also be designed to incorporate a mechanical travel limiter, if desired. In one example as shown in FIGS. 3, 4, 6, and 7, a yolk assembly 122 can be provided as part of the X-axis drive 104. The yolk assembly 122 has a top plate 124 extending over a top of the housing 102. The yolk assembly 122 also has a pair of side plates 126 extending down from the top plate 124. The side plates 126 can be affixed to the upper ends of the drive links or otherwise to the drive shaft 114 of the motor 110, so that the yolk assembly 122 also rotates with the drive shaft. A stop bracket 128 is disposed at one end of the motor 110 adjacent one of the yolk side plates 126. Two stops 130, i.e., fore and aft travel stops protrude upward from the stop bracket 128. The stops 130 are positioned and circumferentially spaced apart relative to the X-axis. The top plate 124 of the yoke assembly 122 is captured between the two stops and hits one of the stops to limit travel of the yoke assembly in either rotation direction. The radius of the side plates 126 and spacing of the stops 130 can thus limit rotational travel of the output shaft 114 to a specific arc, which mechanically limits the upward and downward travel of the tibia rods 98.

The above-described anterior-posterior movement components of the tibia positioning assembly 90 can vary considerably from the example shown and described herein. The yoke assembly 122 and stop bracket 128 can be eliminated or can take on different positions, configurations, and constructions. Instead, another mechanical stop mechanism can be employed. Likewise, the configuration and construction of the drive links 116, cross-plate 120, tibia rods 98, and calf plate 100 can also be varied. The mechanisms or devices that are used to secure a patient's leg to the tibia rods 98 and to the foot plate 92, if and when needed for testing, can also vary.

As shown in FIGS. 4 and 6, the Y-axis drive 106 can also include a second motor, which can also be an electric motor 140, a gearbox 142, and an output shaft 144 that is driven by the motor and gearbox. The gearbox 142 and motor 140 are fixed to the sled assembly 86 beneath the X-axis drive 104. Thus, the entire tibia positioning assembly 90, including the Y-axis drive components, can slide lengthwise along the sub-frame 68 to adjust the foot plate 92 position relative to the table assembly 52 and/or the thigh and knee stabilizers 70, 74. The motor 142 can be secured to a motor mount or bracket 146 that is carried on the sled assembly 86. A Y-axis torque transducer 148 is fixed to the output shaft 144 for rotation therewith. A pivot plate 150 can be sandwiched between a pair of thrust bearings 152 with the Y-axis drive below the pivot plate and the Y-axis torque transducer above the pivot plate. Support brackets 154 are secured to the top of the pivot plate 150 and the torque transducer 146 is fixed to the support brackets. The pivot plate 150 is disposed on top of the motor mounts 146 in this example and can rotate relative to the mounts and the sled assembly 86. The shell 102 can be secured to the pivot plate 150 to create an enclosure for the X-axis drive 104 and the Z-axis drive 108. Thus, as the output shaft 144 is reversibly rotated by the motor 140 and gearbox 142 about the Y-axis, as represented in FIG. 8, the shell 102, pivot plate 150, X-axis drive 104, Z-axis drive 108, foot plate 92, and tibia rods 98 will all rotate about the Y-axis.

Figure 8:
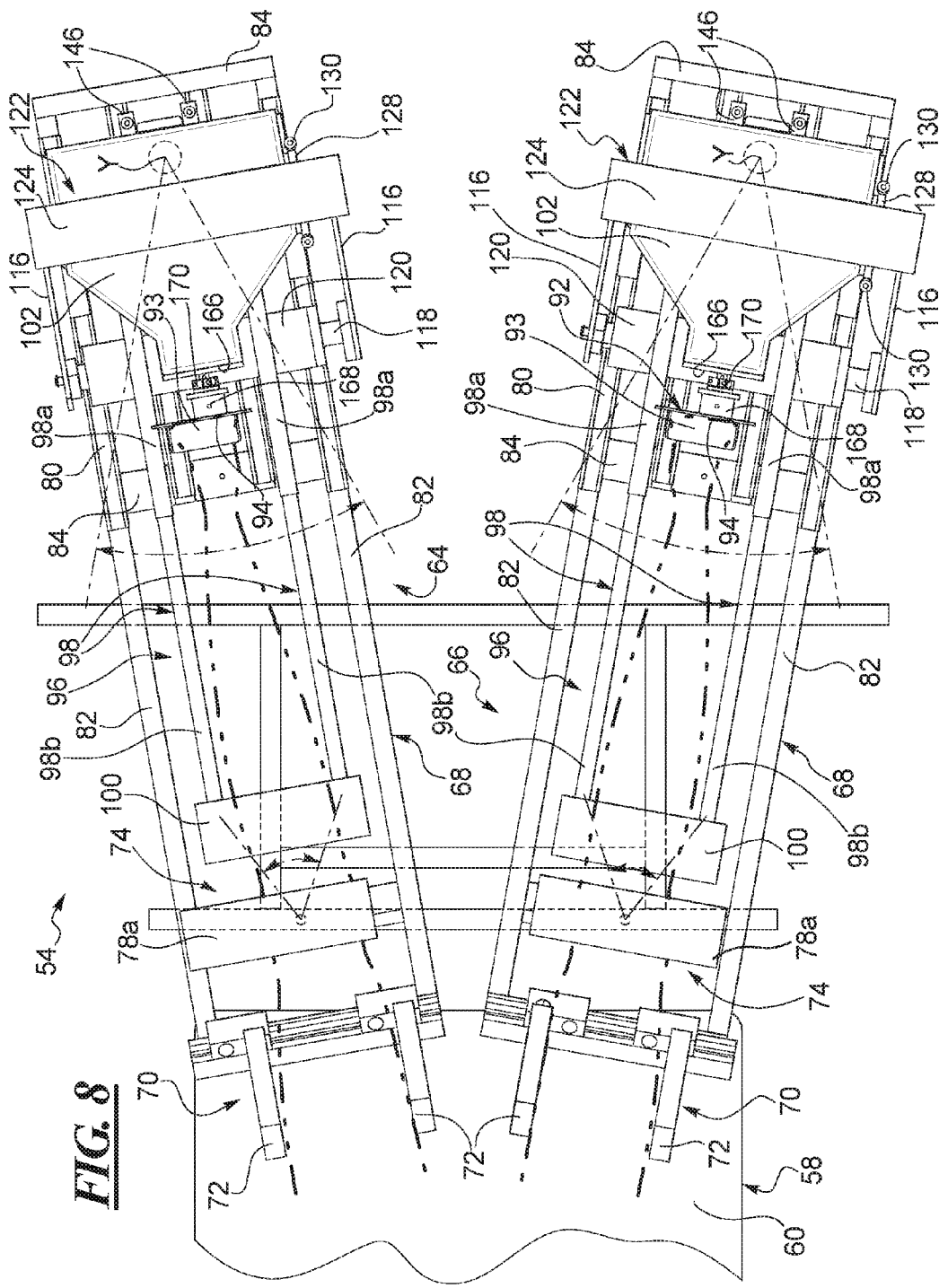
FIG. 8 shows a top view of the robot of FIG. 5 and illustrates Varus-valgus motion of the robot about the Y-axis of each of the left and right leg portions of the robot.

As represented in FIG. 8, the Y-axis drive 106 is configured to conduct a Varus-valgus or V-V test on a patient's knee. Position sensors can be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 8. The motor 140 can reversibly rotate the output shaft 144 through an arc about the Y-axis whereby the pivot plate 150 is rotated through the same arc. This in turn moves, i.e., pivots the Z-axis drive 108 side-to-side, which in turn pivots the foot plate 92 and the tibia rods 98 about the Y-axis. Movement of the tibia rods 98 moves the patient's lower leg side-to-side relative to the femur. The Y-axis torque transducer 148 measures the applied torque at the output shaft 144 caused by the load applied at the calf plate 100 or along the tibia rods as the tibia rods push the patient's tibia medially or laterally relative to the femur. Motion and load data can be collected by a processor from the sensors relative to the motion in the patient's leg and from the Y-axis torque transducer 148 relative to the torque or applied forces.

The motor 140 and/or gearbox 142 can be designed to produce a limited range of travel, which may be substantially less than 360 degrees of rotations, in the output shaft 114. In addition or in the alternative, the Y-axis drive 108 components can also be designed to incorporate a mechanical travel limiter, if desired, though not shown or described herein.

The above-described Varus-valgus movement components of the tibia positioning assembly 90 can also vary considerably from the example shown and described herein. The sled assembly 86, motor mounts 146, pivot plate 150, and support brackets 154 can be eliminated or can take on different positions, configurations, and constructions. For example, the pivot plate 150 can include a curved guide slot 156 formed through the plate, as shown in FIG. 4. The guide slot 156 can be spaced a radial distance from the Y-axis and the output shaft 144 of the motor 140. A guide post 158 can be fixed to the sled assembly 86 and project upward toward the guide slot 156. A tip 159 of the guide post 158 can be captured in or seated in the guide slot and can be configured to both support the pivot plate 150 thereat and to slide along the guide slot as the pivot plate is rotated by the motor 140. Likewise, the configuration and construction of the cross-plate 120, tibia rods 98, calf plate 100, shell 102, and the like can also be varied. The mechanisms or devices that are used to secure a patient's leg to the tibia rods 98 and to the foot plate 92, if and when needed for testing, can also vary.

As shown in FIGS. 4 and 6, the Z-axis drive 108 can also include a third motor, which can also be an electric motor 160, a gearbox 162, and an output shaft 144 that is driven by the motor and gearbox. The gearbox 162 and motor 160 are fixed to a motor mounting bracket 166 that is attached to a front end of the pivot plate 150 and forward of the X-axis drive 104. In this example, the Z-axis is aligned with both the X-axis and the Y-axis, though in other examples this might not be the case. The entire Z-axis drive, including the foot plate 92, can also slide lengthwise along the sub-frame 68 to adjust the foot plate 92 position relative to the table assembly 52 and/or the thigh and knee stabilizers 70, 74 as noted above. A Z-axis torque transducer 168 is fixed to the output shaft 164 by an adaptor 170 for rotation therewith. In this example, the motor 160 and gearbox 162 are positioned behind the motor mounting bracket 166 and the adaptor 170 and torque transducer 168 are disposed forward of the mounting bracket. The enclosure defined by the shell 102 and the pivot plate 150 house the Z-axis drive 108, other than the foot plate 92, as noted above. The foot plate 92 is secured to the torque transducer 168 for rotation therewith. Thus, as the output shaft 164 is reversibly rotated by the motor 160 and gearbox 162 about the Z-axis, as shown in FIG. 9, the foot plate 92 will all rotate about the Z-axis.

Figure 9:
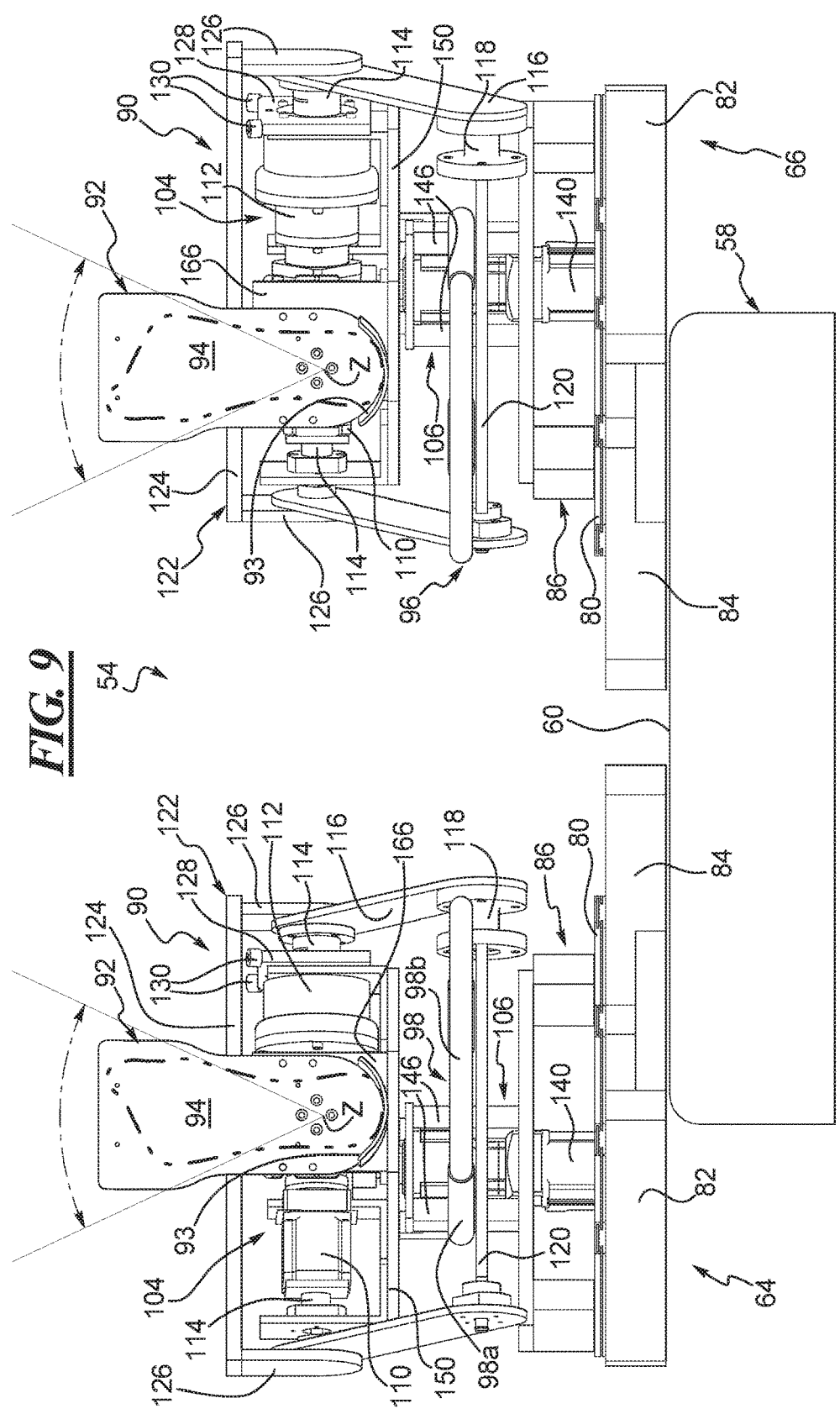
FIG. 9 shows an end view of the robot of FIG. 5 from the point of view and in the direction of the arrow IX and illustrates internal and external rotation of the robot about the Z-axis of each of the left and right leg portions of the robot.

As represented in FIG. 9, the Z-axis drive 108 is configured to conduct an internal and external rotation or simply a tibia rotation test on a patient's knee. Position sensors can be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 9. The motor 160 can reversibly rotate the output shaft 164 through an arc about the Z-axis whereby the adapter 170 and torque transducer 168 are rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque at the output shaft 164 caused by the load applied at the foot plate 92 as the foot plate rotates the patient's tibia or lower leg internally and externally relative to the femur. Motion and load data can be collected by a processor from the sensors relative to the motion in the patient's leg and from the Z-axis torque transducer 168 relative to the torque or applied forces.

The motor 160 and/or gearbox 162 can be designed to produce a limited range of travel, which may be substantially less than 360 degrees of rotations, in the output shaft 164. In addition or in the alternative, the Z-axis drive 108 components can also be designed to incorporate a mechanical travel limiter, if desired. A simple mechanical stop can be positioned to stop movement of the foot plate 92 in either rotation direction, if desired. Such a sop can be the tibia rods 98 or something mounted thereto. Alternatively, such a stop can be applied to the motor mounting bracket 166 or the like.

The above-described rotation movement components of the tibia positioning assembly 90 can also vary considerably from the example shown and described herein. The foot plate 92 and motor mounting bracket 166 can be eliminated or can take on different positions, configurations, and constructions. The mechanisms or devices that are used to secure a patient's leg to the foot plate 92, if and when needed for testing, can also vary.

The above described motors, gearboxes, and output shafts can also vary within the scope of the disclosure. The motors can be servo-motors or other types of motors suitable for precise motion and torque control and for the loads to which the motors will be exposed during such limb testing and evaluation. Any of the first, second, or third, i.e., X-, Y-, or Z-axis, drives with respect to the motors and gearboxes can be structurally configured substantially the same relative to one another, with the only substantive difference being the relative axis of rotation about which each is oriented. Alternatively, each drive can incorporate a motor and/or gearbox that is different than one or both of the others as well. The torque transducers can be selected in order to provide torque readings as known in the art relating to each of the three drives. In other examples, one or more of the torque transducers may be replaced with other torque or load sensors or load sensing means. For example, motor current may be measured to determine the torque or load on the motor output shaft during use. Any suitable means for modeling torque may be used. The torque readings can be calibrated and calculated as needed to correspond to known torque or force values imparted to a patient's limb(s). Movement of the patient's body parts may be detected by non-invasive systems, as noted above, that utilize sensors or markers that are attached to the skin, including but not limited to vision, optoelectronic, ultrasonic, and electromagnetic motion analysis systems.

In use, a patient lies on the padded surface 60 of the platform 58 on the table assembly 52 as shown in FIG. 5. The patient's knees are positioned to engage the knee stabilizers 74, their thighs are positioned to engage the thigh stabilizers 70, their feet are positioned to engage the foot plates 92, and their calves are positioned to engage the tibia rods. The patient can then be secured to the foot plates, to the knee stabilizers, and to the thigh stabilizers for testing and evaluation. The patient's calves or tibias can also be secured to the tibia rods 98, as needed for specific testing. Movement of the lower leg of the patient may be detected by non-invasive systems utilizes sensors or markers that are attached to the skin, including but not limited to optoelectronic, ultrasonic, and electromagnetic motion analysis systems. In one example, the RKT apparatus can be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion.

Any one of the X-, Y-, and Z-drives can be decoupled from any of the other two. In the disclosed example, each of the three drive assemblies may be operable with one or more of the other at the same time or can be decoupled from each of the other two and be operable independent of the other two. In other examples, two or more, and perhaps all three of the drives can be mutually coupled relative to one another such that movements are substantially simultaneously imposed upon the patient's legs during use of the RKT apparatus. The combined simultaneous operation of two or all three of the motors allows the RKT apparatus to perform more complex testing, such as simulating the known manual pivot shift testing procedure.

The aforementioned sensors can be provided on the legs of a patient, in the power lines of the RKT apparatus, and/or on the X-, Y-, and Z drives to obtain desired position or location data as the lower leg is moved during testing and evaluation. The degree of movement of the patient's legs in the A-P test, the V-V test, and/or the rotation test can be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded. Various X-, Y-, and Z-axes can also be determined and recorded for and/or relating to the femoral and tibial axis of the patient for testing.

Figure 10:
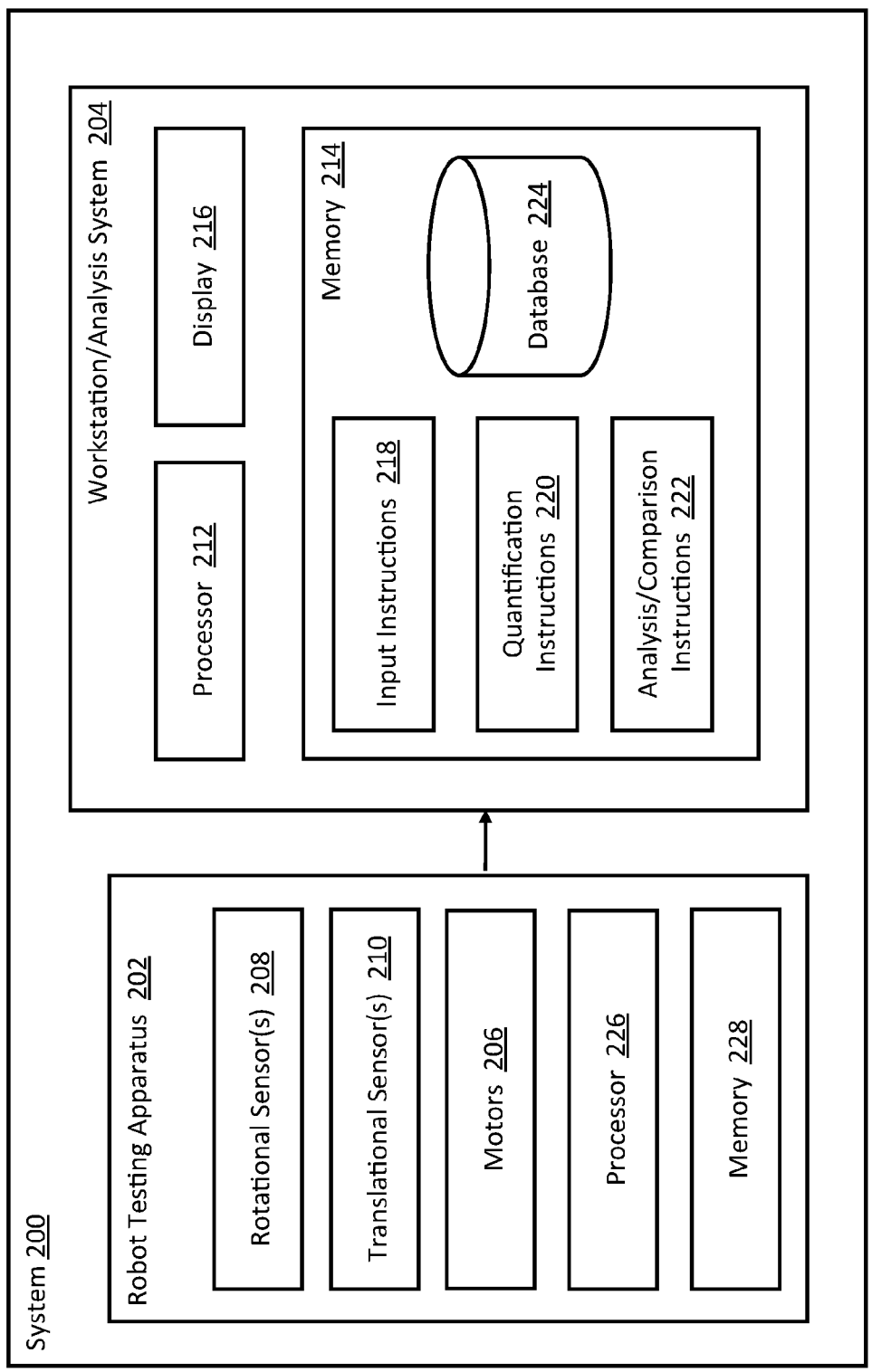
FIG. 10 is a block diagram of a system for quantification and evaluation of joint play in accordance with one example.

FIG. 10 illustrates a system 200 directed to quantification and evaluation of joint play. In this example, the system 200 includes a robot testing apparatus 202 and an analysis system 204 in communication with the robot testing apparatus 202. The analysis system 204 may be a workstation or other computer coupled to the robot testing apparatus 202. In this example, the communications and coupling between the robot testing apparatus 202 and the analysis system 204 are directed to providing data acquired by the robot testing apparatus 202 to the analysis system 204. Alternatively or additionally, the communications are directed to allowing the analysis system 204 to control one or more aspects or features of the robot testing apparatus 202.

The robot testing apparatus 202 is configured to implement rotational joint testing and translational joint testing of a joint. The robot testing apparatus 202 implements the rotational and translational joint testing to acquire or capture rotational and translational data indicative of rotational and translational movement of the joint during the rotational and translational joint testing, respectively. For instance, in implementing such testing, the robot testing apparatus 202 may be configured to detect a range of rotational motion and a range of translational motion for the joint. Other types of data indicative of rotational and translational movement of the joint during the rotational and translational joint testing may be acquired. For instance, the rotational and translational data acquired by the robot testing apparatus 202 may be indicative of a position (e.g., a relative position) of the joint for a given torque level.

Various types of rotational and translational joint testing may be implemented by the robot testing apparatus 202. In examples in which the joint is a knee, the rotational movement may be or include external-internal rotational movement and/or varus-valgus rotational movement. The translational movement may be or include anterior-posterior movement. Additional and/or alternative rotational and/or translational movements may be measured. The number of different rotational and translational joint tests implemented by the robot testing apparatus 202 may vary accordingly.

The robot testing apparatus 202 includes a number of motors 206, one or more sensors 208 directed to capturing data for the rotational joint testing ("rotational sensors"), and one or more sensors 210 directed to capturing data for the translational joint testing ("translational sensors"). Each sensor 208, 210 is configured to capture data indicative of position as the rotational and translational joint testing is implemented. The motors 206, the rotational sensor(s) 208, and the translational sensor(s) 210 may be otherwise configured as described above in connection with FIGS. 1-9. Also as described above, each motor 206 may include a torque transducer or sensor to capture data indicative of the torque level applied to the joint during the rotational and translational joint testing.

The analysis system 204 includes a processor 212 and a memory 214 for processing the data captured by the robot testing apparatus 202. The processor 212 is coupled to, or otherwise in communication with, the robot testing apparatus 202. In this example, the analysis system 204 also includes a display 216 for providing a user interface for an operator of the analysis system 204. The user interface may be directed to controlling the robot testing apparatus 202 and/or the analysis system 204. The user interface may be alternatively or additionally directed to presenting the results of the processing.

The processor 212 is coupled to the memory 214 to access instructions and/or other data stored on the memory 214. In the example of FIG. 10, input instructions 218, quantification instructions 220, and analysis instructions 222 are stored on the memory 214. The instructions 218, 220, 222 may be stored as one or more modules or instruction sets, and may be integrated to any desired extent. The memory 214 may have additional data stored thereon, such as load-deformation data of the joint under test or other joint instances. The memory 214 may be or include any number of storage devices, memories, and/or other computer-readable media.

The processor 212 is configured through execution of the input instructions 218 to obtain the rotational and translational data captured via the robot testing apparatus 202. In some cases, the input instructions 218 cause the processor 212 to request the rotational and translational data from the robot testing apparatus 202. In other cases, the data may be received (e.g., provided) without a request. For instance the input instructions 218 may cause the processor 212 to access the memory 214 to obtain the translational and rotational data.

The rotational and translational data may thus be obtained in additional and/or alternative ways. For instance, the processor 212 may be configured to obtain raw sensor data from the robot testing apparatus 202 for the rotational and translational joint testing. The input instructions 218 (and/or other instructions) may then cause the processor 212 to process the raw sensor data to develop rotational data indicative of the range of rotational motion and translational data indicative of the range of translational motion. The extent to which the data provided to the processor 212 is processed before analysis may vary.

The input instructions 218 may cause the processor 212 to obtain rotational and translational data for various types of rotational and translational joint testing. In one knee-based example, the input instructions 218 configure the processor 212 to obtain rotational data indicative of external-internal rotational movement of the knee and rotational data indicative of varus-valgus rotational movement of the knee. Fewer, alternative, or additional rotational data may be obtained. For example, the rotational data obtained may be indicative of varus-valgus rotational movement. In the one knee-based example, the translational data is indicative of anterior-posterior translational movement of the knee. Alternative or additional translational data may be obtained. For example, the translational data may be indicative of movement along a different direction or axis than the direction or axis along which anterior-posterior movement occurs.

The processor 212 is configured through execution of the quantification instructions 220 to compute a quantity indicative of the joint play of the joint. The quantification instructions 220 may cause the processor 212 to combine or synthesize the rotational and translational data. The combination may be considered a synthesis because of the different nature of the rotational and translational data. For instance, the rotational and translational data may have different units. The rotational data may be presented in degrees or radians, while the translational data may be presented in units of distance. The computation involving such disparate units may accordingly result in a quantity synthetically indicative of joint play.

The quantification instructions 220 may cause the processor 212 to compute the joint play quantity via a function of the rotational data and the translational data. The function takes the rotational and translational data as arguments or inputs. For example, the ranges of rotational and translational movement for the rotational and translational joint testing may be input parameters of the function.

The function specified by the quantification instructions 220 specifies or includes a combination of the rotational and translational data. In some cases, the combination forms a multiplication product of the rotational and translational data. For instance, in one knee-based example, the quantity computed multiplies the ranges of motion for one rotational joint test (e.g., external-internal rotation or varus-valgus rotation) and one translational joint test (e.g., anterior-posterior translation). With the two movements being, in a sense, orthogonal, the resulting quantity may be considered an area, or joint play area. In another knee-based example, the computation function takes the ranges of external-internal rotation, varus-valgus rotation, and anterior-posterior translation as operands. The resulting quantity may be considered a volume, or joint play volume. The operands of the multiplication product may include any combination of the data representative of the motion detected in any of the six degrees of freedom captured during testing, the six degrees of freedom being the translations along the three axes and the rotations about the three axes.

The quantification instructions 220 are not limited to the above-described joint play area and volume quantities. Other combinations of the rotational and translational data may be computed through multiplication. For instance, other functions multiplying the values of two or more ranges may be used to synthetically combine the rotational and translational data. A wide variety of quantities may thus be considered to be synthetically or artificially indicative of joint play. The multiplication computation may include fewer, additional, and/or alternative operands. For example, the operands include a coefficient or other factor to be added, multiplied, or otherwise applied to the rotational and translational data.

The joint play quantity may be synthesized or computed via other combinations of the rotational data and the translational data with or without involving a multiplication computation. For instance, the function may include operators in addition or alternative to multiplication (e.g., addition). In some cases, the function may include an offset that adds or subtracts an amount from the quantity in view of various effects or conditions. The function may differ in still further ways. For instance, the function may be a polynomial function having terms of various orders. As an example, a term of the polynomial function may involve the translational data squared, or raised to the second power.

The operands or other input parameters of the function may be indicative of the rotational or translational movement in ways other than a range of motion (e.g., maximum range of motion). For instance, the function may take as an input data indicative of travel in a single direction (e.g., external rotation) under a given load. The given load may vary based on other factors, including factors specific to the joint type or subject.

The processor 212 is configured through execution of the analysis instructions 222 to determine whether the computed joint play quantity exceeds a joint play threshold. The computed quantity may be compared with the joint play threshold to determine whether the synthesized or combined rotational and translational data is indicative of a joint abnormality. The determination may alternatively or additionally be directed to whether the data is indicative of an injured joint or a joint for which surgery or other treatment is warranted.

The comparison of the computed joint play quantity and the joint play threshold establishes a unilateral or single factor assessment of joint play or laxity. If the threshold is not exceeded, then the analysis instructions 222 may cause the processor 212 to generate or otherwise provide an output indicative of a joint free of abnormalities. The output or other indication may be provided via the display 216. On the other hand, if the threshold is exceeded, then the analysis instructions 222 may cause the processor 212 to implement further analysis in an effort to identify one or more joint abnormalities underlying the excessive computed joint play quantity.

The processor 212 is further configured through execution of the analysis instructions 222 to compare or otherwise analyze the individual, or constituent, rotational and translational data obtained for the joint with preset data for the rotational and translational joint testing. The rotational and translational data may correspond with the data underlying the computed joint play quantity. The data underlying the computed joint play quantity may include the rotational data and the translational data used to compute the quantity.

Preset data is stored in a database 224 for each constituent test. In this example, the memory 214 includes the database 224. Any data store or data structure may be used. For example, the database 224 may be or include a computer-readable storage device or other memory (e.g., a database server) remote from the remainder of the memory 214. The preset data includes both preset rotational data and preset translational data. The preset data may be, include, or be based on historical or other data previously acquired for the joint testing. The preset data may include data for both normal and abnormal joints. In some cases, the preset data includes rotational and translational thresholds for the rotational and translation joint testing. For example, the preset data includes a threshold that establishes a maximum range of motion for external-internal rotation. The preset data may include similar thresholds for each type of joint test for which data is available for the joint being evaluated. Other types of thresholds may be used. For example, one or more thresholds may be based on a standard deviation from a mean or average range of motion for a subject with similar characteristics (e.g., height, weight, age, etc.).

The preset data for the joint tests may vary from example to example, as well as from test to test. Various types of thresholds may be used. In some cases, one or more thresholds are based on a mean and standard deviation for the joint testing. Alternatively or additionally, the preset data may be or include a distribution and/or a range (e.g., a pair of endpoints). Each distribution may present the range of motion for a number of previously tested joints. Where a particular joint falls along the distribution may be indicative of whether the test result is considered normal or abnormal. Other types of datasets may be used to analyze the rotational and translational data. For example, the preset data may be indicative of boundaries (e.g., range of motion boundaries) between abnormal and normal joints.

In some cases, the rotational and/or translational data used by the analysis instructions 222 includes data that was not relied upon to compute the joint play quantity. For example, in cases in which the joint play quantity is an area, the joint play quantity may be computed through multiplication of data indicative of the varus-valgus rotational range of motion and the anterior-posterior translational range of motion. The analysis instructions 222 may then, in turn, compare or analyze data indicative of the external-internal rotation range of motion. Such analysis may be in addition to the analysis of the data from the other constituent joint tests (e.g., varus-valgus rotation and anterior-posterior translation).

In some cases, it is possible that the analyses for all of the individual tests result in a normal finding. The joint under test may pass all of the tests despite an initial finding of an excessive joint play quantity. In such cases, the analysis instructions 222 may configure the processor 212 to provide an indication that the joint is normal or sufficiently normal. Examples of sufficiently normal joints include joints that are not injured, joints that do not warrant surgery, and joints that do not warrant other treatment or further analysis (e.g., imaging).

For joints having one or more tests having an abnormal finding or result, the processor 212 may be further configured through execution of the analysis instructions 222 for reporting and/or further analysis. In some cases, the analysis instructions 222 may cause the processor 212 to identify the one or more tests having the abnormal finding. For example, the processor 212 provides a report that indicates that the range of varus-valgus rotation for the joint fell outside of a normal distribution. A clinician or physician may then use the report to identify an injury and/or appropriate surgery or other treatment or course of action (e.g., imaging).

The further analysis may be directed to identifying an injury, surgery, treatment, or other course of action. To that end, the further analysis includes accessing data stored in the memory 214, such as the database 224. In some cases, the data is profile data for abnormal joints. The profile data includes profiles for each type of joint abnormality. For example, the profile data may include data indicative of the results or findings for each individual test for joints having a torn ACL. A torn ACL may thus be represented by an abnormal anterior-posterior test with increased anterior translation, or an abnormal external-internal rotation test with increased internal rotation. The profile data may alternatively or additionally indicate whether one or more tests do not show an abnormal test result. In other cases, profiles may indicate an extent to which the test has an abnormal finding. For example, the profile data may distinguish between tests having a slightly abnormal result and a significantly abnormal result. Distribution, threshold, and/or other data in the database 224 may be used to characterize the extent of the abnormality. The test results may be characterized and distinguished in other ways. For example, test results may be characterized as indicative of a low, medium, or high abnormality.

The further analysis may compile the results of the individual tests into a profile for the joint under test. The profile of the joint may thus be indicative of the results of the comparisons of the rotational data and the translational data with, for instance, rotational and translational thresholds.

The analysis instructions 222 may cause the processor 212 to incorporate other data into the profile. For example, the profile may include height, weight, and other data indicative of the subject. The computed joint play quantity may also be incorporated into the profile. Any data that may be helpful to identifying a joint abnormality may be incorporated. For example, the profile data may specify data indicative of the bones that define the joint under test, such as structural characteristics of the bones, the three-dimensional surfaces of the bones, and the contact points between the bones. Any of these or other parameters may be involved in the analysis (e.g., comparison with the profile data) of the profile of the joint under test implemented via the analysis instructions 222.

In some examples, the processor 212 is configured through execution of the analysis instructions 222 to assess the profile to identify an abnormality of the joint under test. The assessment may include comparing the profile with the profile data to find one or more matches or closest matches. The profile data may have been generated using the same testing apparatus (or type of testing apparatus) used to acquire data for the joint under test. In that way, the patient set-up and other factors underlying the data acquisition are consistent across the joint instances. A profile match may identify multiple abnormalities.

The analysis system 204 and the robot testing apparatus 202 may be integrated with one another to any desired extent. In the example of FIG. 10, the robot testing apparatus 202 includes a processor 226 and a memory 228. The processor 226 and the memory 228 may be dedicated to supporting the data acquisition and communication functions of the robot testing apparatus 202. For instance, the processor 226 and the memory 228 may not be configured to implement the quantification and evaluation aspects of the system 200. In other cases, the processor 226 and the memory 228 are involved in the execution of the input instructions 218, quantification instructions 220, and/or the analysis instructions 222. In still other cases, the robot testing apparatus 202 and the analysis system 204 share one or more processing and/or memory components.

Each processor 212, 226 may be or include any number or type of processing cores, processors, processing units (e.g., a central processing unit or graphical processing unit), or processing systems. Each processor 212, 226 may be a component in a variety of systems. For example, each processor 212, 226 may be part of a standard personal computer or a workstation. Each processor 212, 226 may be or include one or more general processors, digital signal processors, application specific integrated circuits, field programmable gate arrays, servers, networks, digital circuits, analog circuits, combinations thereof, or other now known or later developed devices for analyzing and processing data.

Each memory 214, 228 may be or include any number or type of computer-readable memories, media, or other devices on which data is stored. Each memory 214, 228 may be or include a main memory, a static memory, or a dynamic memory. Each memory 214, 228 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, each memory 214, 228 may include a cache or random access memory for a processor. Alternatively or additionally, each memory 214, 228 may be separate from the processor, such as a cache memory of a processor, the system memory, or other memory. Each memory 214, 228 may be or include an external storage device or database for storing data. Examples may include a hard drive, compact disc ("CD"), digital video disc ("DVD"), memory card, memory stick, floppy disc, universal serial bus ("USB") memory device, or any other device operative to store data. Each memory 214, 228 may be operable to store instructions executable by a processor. The functions, acts or tasks illustrated in the figures or described herein may be performed by the programmed processor executing the instructions stored in the memory 214, 228. The functions, acts or tasks may be independent of the particular type of instruction set, storage media, processor or processing strategy and may be performed by software, hardware, integrated circuits, firmware, micro-code and the like, operating alone or in combination. Likewise, processing strategies may include multiprocessing, multitasking, parallel processing and the like.

Figure 11:
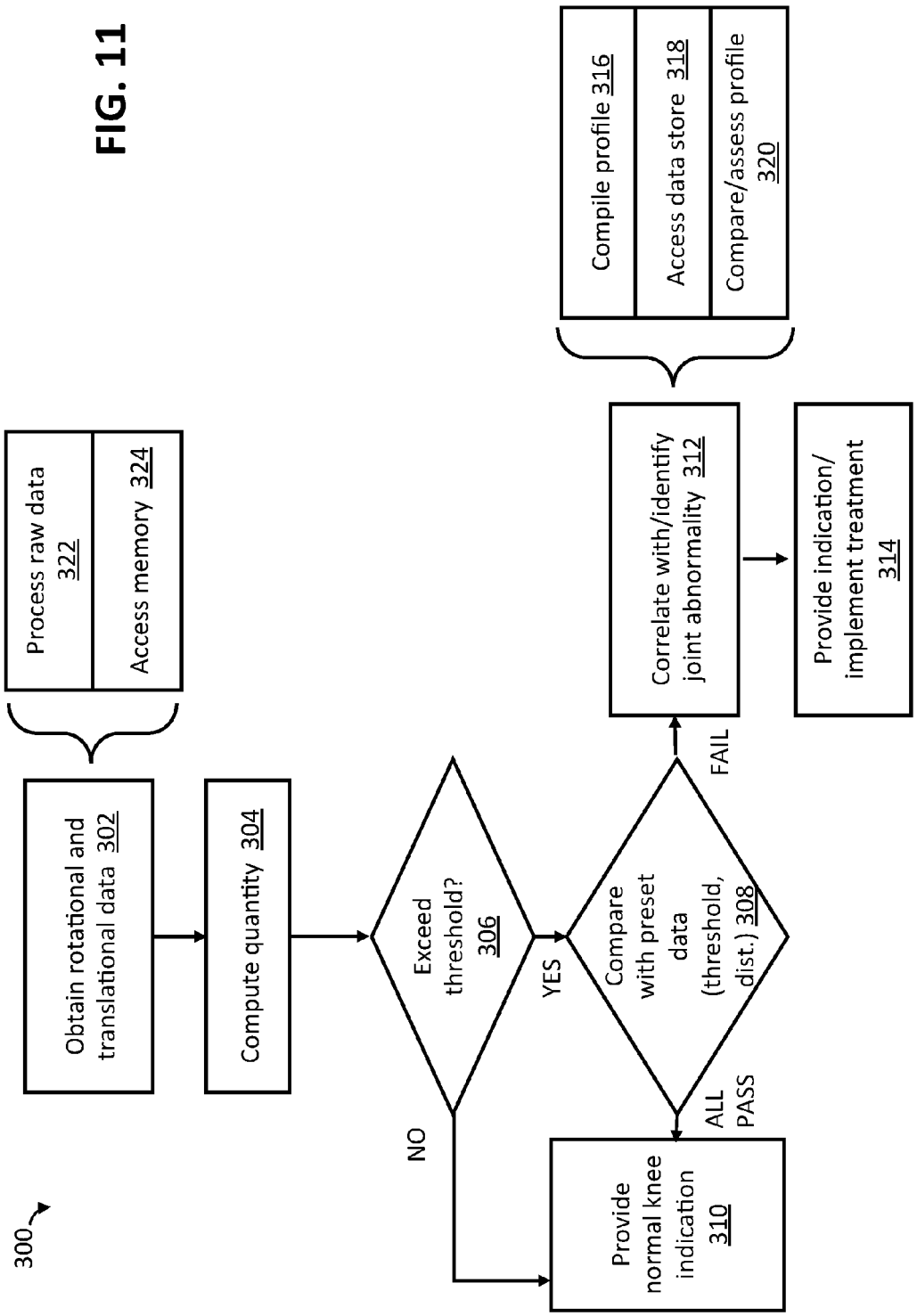
FIG. 11 is a flow diagram of a method for quantification and evaluation of joint play in accordance with one example.

FIG. 11 depicts a method 300 of quantifying and evaluating joint play. The method 300 is computer-implemented. The method 300 may be implemented by the system 200 of FIG. 10. In some cases, for instance, the processor 212 (FIG. 10) implements one or more acts of the method 300. Alternatively or additionally, the processor 226 (FIG. 10) of the robot testing apparatus 202 implements one or more acts of the method 300. In these cases, the processor 212 and/or the processor 226 are configured via execution of computer-readable instructions, such as the instructions 218, 220, 222 (FIG. 10) stored in the memory 214 (FIG. 10), to cause the processor 212, 226 to implement the method 300. The method 300 may be implemented in additional and/or alternative ways. For instance, one or more acts of the method 300 may be implemented by a remote processor, such as a processor in communication with the processor 212 and/or the processor 226.

The method 300 includes an act 302 in which rotational and translational data is obtained. The rotational and translational data is indicative of rotational and translational movement of the joint during rotational and translational joint testing, respectively. The rotational and translational joint testing is implemented by a robotic testing apparatus applied to the joint, such as the apparatus described above. In some cases, the rotational data and the translational data are indicative of a rotational range of motion and a translational range of motion achieved by the joint during the rotational and translational joint testing, respectively. Additional or alternative types of data may acquired. For instance, the data may be indicative of a displacement for a given force or torque level. In cases in which the joint is a knee, the rotational movement may be or include varus-valgus rotational movement of the knee and/or external-internal rotational movement of the knee.

The joint play quantity is computed in an act 304. As described above, the joint play quantity may be indicative of the laxity of the joint. The joint play quantity may be computed via synthesis or combination of the rotational and translational data. In some cases, the joint play quantity is computed via a function of the rotational data and the translational data. For instance, the function forms a multiplication product of the rotational data and the translational data. The joint play quantity may thus be considered a joint play area, as described above. In knee cases in which two rotational movement tests are implemented, the multiplication function may also take further rotational data as an input. The joint play quantity may be considered a joint play volume, as described above.

A decision block 306 determines whether the computed quantity exceeds a joint play threshold. The threshold comparison may be used to determine whether the joint play quantity is indicative of a joint abnormality. As described above, a determination that the computed joint play quantity exceeds the joint play threshold is a prerequisite or gateway to identifying the abnormality.

Control passes to another decision block 308 if the computed joint play quantity exceeds the joint play threshold. The decision block 308 compares the rotational data and the translational data with preset rotational data and preset translational data for the rotational and translation joint testing, respectively. The joint play threshold may be at a level such that quantities above the joint play threshold are indicative of an abnormality that should be identified or characterized. In the example of FIG. 11, however, the joint play threshold is at a level that still allows for the possibility that the joint is normal (e.g., is not injured, does not warrant surgery or other treatment, or does not warrant further analysis). Either way, the comparison may be directed to identifying, categorizing, or otherwise characterizing an abnormality of the joint.

As described above, the preset rotational data and the preset translational data are indicative of rotational and translational ranges of motion, respectively, for the rotational and translational joint testing, in some cases. The ranges of motion of the preset rotational data and the preset translational data may include respective distribution datasets. Alternatively, the preset data for each joint test may be or include one or more thresholds, boundaries between normal and abnormal joints, and/or other data, as described above.

In the example of FIG. 11, if either the joint play threshold is not exceeded, or if all of the comparisons of the individual tests pass the comparison of the block 308, control passes to a block 310 in which an indication of a normal joint (knee) is provided. The indication may be provided via a display. The indication may be provided in other ways. For example, a message may be generated and transmitted to a clinician, physician, or other user.

If at least one of the comparisons with the preset data fails, then control passes to a an act 312 to identify one or more joint abnormalities. The identification is based on which the results of the tests or comparisons. For example, the results of the comparisons are correlated with the profile data for the joint abnormality(ies). If the profile data matches (or sufficiently matches) the results of the comparisons, then the abnormality associated with that profile is identified as applicable to the joint under test. An indication of the identified joint abnormality is then provided in an act 314. The indication alternatively or additionally includes a recommended treatment or other course of action. The act 314 may thus include implementing the recommended treatment in some cases.

In the example of FIG. 11, the act 312 includes an act 316 in which a profile is compiled for the joint under test. The profile may be indicative of the results of comparing the rotational and the translational data with the preset rotational and translational data. The profile may include other types of data, such as characteristics of the subject and the computed joint play quantity, as described above. A data store, such as the database 224 (FIG. 10) is then accessed to obtain the profile data for various abnormalities. The profile is then assessed in an act 320 through, e.g., a comparison of the profile and the abnormality profile data.

The act 302 may include an act 322 in which raw data provided by the robot testing apparatus is processed. The processing may include, for example, determining ranges of motion from the raw data. The processing may vary with the nature of the data used to compute the joint play quantity. Alternatively or additionally, the raw data is already processed into the rotational and translational data to be used to compute the joint play quantity. In such cases, the act 302 includes an act 324 in which a memory is accessed to obtain the range of motion data for each joint test, and/or other rotational and translational data. In still other cases, the act 302 includes acquiring or capturing the raw data.

The methods described herein may be implemented by software programs executable by a computer system. Further, implementations may include distributed processing, component/object distributed processing, and parallel processing. Alternatively or additionally, virtual computer system processing may be constructed to implement one or more of the methods or functionality as described herein.

As described above, a number of measured factors may be synthesized or combined into a joint play quantity. The measured factors may be or include data from multiple single plane tests, such as those described herein. The joint play quantity is a repeatable biomechanical measurement that correlates highly with patient satisfaction and/or provides an effective diagnostic screening tool. For example, the joint play quantity can better predict whether a patient will be satisfied after a ligament reconstruction than any other individual factor (e.g., pivot shift test results). The joint play quantity is better at grouping all the unsatisfied patients together and is therefore a better predictor of patient satisfaction. The joint play quantity may thus provide a single factor used in an assessment of the joint. As described above, the assessment may use the joint play factor as a prerequisite or gateway to further analysis of the joint.

The computer-readable media referenced above may be a single medium or multiple media, such as a centralized or distributed database, and/or associated caches and servers that store one or more sets of instructions. The term "computer-readable medium" may also include any tangible medium that may be capable of storing, encoding or carrying a set of instructions for execution by a processor or that may cause a computer system to perform any one or more of the methods or operations disclosed herein. Such computer-readable media may be referred to as "computer-readable storage media."

The computer-readable medium may include a solid-state memory such as a memory card or other package that houses one or more non-volatile read-only memories. The computer-readable medium also may be a random access memory or other volatile re-writable memory. Additionally, the computer-readable medium may include a magnetooptical or optical medium, such as a disk or tapes or other storage device. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or additionally, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of evaluating a joint, the method comprising:
   obtaining, by a processor, rotational data and translational data captured via a robotic testing apparatus for the joint, the rotational and translational data being indicative of rotational and translational movement of the joint, respectively, during rotational and translational joint testing, the rotational and translational joint testing being implemented by the robotic testing apparatus applied to the joint, the robotic testing apparatus comprising a plurality of motors for the rotational and translational joint testing, the rotational data and the translational data being indicative of one or more rotational ranges of motion and one or more translational ranges of motion, respectively, for the rotational and translational joint testing;
   computing, by the processor, a quantity indicative of a joint play volume of the joint, the quantity being computed via a function, the function comprising a multiplication of the one or more rotational ranges of motion and the one or more translational ranges of motion for the rotational data and the translational data;
   determining, by the processor, whether the joint has an abnormality by determining whether the computed quantity exceeds a joint play volume threshold;
   if the computed quantity exceeds the joint play volume threshold, comparing, by the processor, the rotational data and the translational data with preset rotational data and preset translational data for the rotational and translation joint testing, respectively, to identify the abnormality of the joint; and
   wherein determining that the joint has an abnormality based on the computed quantity is a prerequisite to identifying the abnormality, such that comparing the rotational data and the translational data with the preset rotational data and the preset translational data is implemented after determining that the computed quantity exceeds the joint play volume threshold.

2. The method of claim 1, further comprising:
   compiling a profile of the joint indicative of results of comparing the rotational and the translational data with the preset rotational and translational data; and
   assessing the profile to identify the abnormality of the joint.

3. The method of claim 2, wherein compiling the profile comprises incorporating the computed quantity into the profile.

4. The method of claim 2, wherein compiling the profile comprises incorporating data indicative of structural characteristics of bones defining the joint.

5. The method of claim 2, wherein compiling the profile comprises incorporating data indicative of three-dimensional surfaces of bones defining the joint.

6. The method of claim 2, wherein compiling the profile comprises incorporating data indicative of contact points between bones defining the joint.

7. The method of claim 2, wherein assessing the profile comprises:
   accessing a data store in which profile data for abnormal joints is stored; and
   comparing the profile with the profile data.

8. The method of claim 1, wherein the preset rotational data and the preset translational data are indicative of rotational and translational ranges of motion, respectively, for the rotational and translational joint testing.

9. The method of claim 8, wherein the rotational and translational ranges of motion are indicative of boundaries between normal joints and abnormal joints.

10. The method of claim 1, wherein the joint is a knee, and wherein the rotational movement comprises varus-valgus rotational movement of the knee.

11. The method of claim 10, wherein the rotational movement further comprises external-internal rotational movement of the knee.

12. The method of claim 1, wherein the preset rotational data and the preset translational data comprise respective distribution datasets.

13. A system for evaluating a joint, the system comprising:
   a memory in which input instructions, quantification instructions, and analysis instructions are stored; and
   a processor coupled to the memory and configured through execution of the input instructions to obtain rotational data and translational data captured via a robotic testing apparatus for the joint, the rotational and translational data being indicative of ranges of rotational and translational motion of the joint, respectively, during rotational and translational joint testing, the rotational and translational joint testing being implemented by the robotic testing apparatus applied to the joint, the robotic testing apparatus comprising a plurality of motors for the rotational and translational joint testing, the rotational data and the translational data being indicative of one or more rotational ranges of motion and one or more translational ranges of motion, respectively, for the rotational and translational joint testing;

wherein the processor is configured through execution of the quantification instructions to compute a quantity synthetically indicative of a joint play volume of the joint via synthesis of the rotational data and the translational data, the synthesis comprising a multiplication of the one or more rotational ranges of motion and the one or more translational ranges of motion for the rotational data and the translational data, wherein the processor is configured through execution of the analysis instructions to determine whether the joint has an abnormality by determining whether the computed quantity exceeds a joint play volume threshold, wherein the processor is configured through execution of the analysis instructions, if the computed quantity exceeds the joint play volume threshold, to compare the rotational data and the translational data with rotational and translational thresholds for the rotational and translational joint testing, respectively, to identify the abnormality of the joint, and wherein a determination that the joint has an abnormality based on the computed quantity is a prerequisite to identifying the abnormality, such that a comparison of the rotational data and the translational data with the rotational and translational thresholds is implemented after the determination that the computed quantity exceeds the joint play volume threshold.

14. The system of claim 13, wherein the processor is configured through execution of the analysis instructions to:
compile a profile of the joint indicative of results of comparing the rotational data and the translational data with the rotational and translational thresholds; and
assess the profile to identify the abnormality of the joint.

15. The system of claim 14, wherein the processor is configured through execution of the analysis instructions to incorporate the computed quantity into the profile.

16. The system of claim 14, wherein the processor is configured through execution of the analysis instructions to:
access the memory to obtain profile data for abnormal joints; and
compare the profile with the profile data.

17. The system of claim 13, wherein the joint is a knee, and wherein the rotational movement motion comprises varus-valgus rotational movement of the knee.

18. The system of claim 17, wherein the rotational motion further comprises external-internal rotational movement of the knee.

19. A system for evaluating a joint, the system comprising:
a robot testing apparatus configured to implement rotational joint testing and translational joint testing of the joint and further configured to detect one or more ranges of rotational motion and one or more ranges of translational motion for the joint, the robotic testing apparatus comprising a plurality of motors for the rotational and translational joint testing;
a memory in which input instructions, quantification instructions, and analysis instructions are stored; and
a processor in communication with the robot testing apparatus and coupled to the memory;

wherein the processor is configured through execution of the input instructions to obtain, via the robot testing apparatus, rotational data indicative of the one or more ranges of rotational motion and translational data indicative of the one or more ranges of translational motion, wherein the processor is configured through execution of the quantification instructions to compute a quantity indicative of a joint play volume of the joint, the quantity being computed via a function, the function comprising a multiplication of the one or more rotational ranges of motion and the one or more translational ranges of motion for the rotational data and the translational data, wherein the processor is configured through execution of the analysis instructions to determine whether the joint has an abnormality by determining whether the computed quantity exceeds a joint play volume threshold, wherein the processor is further configured through execution of the analysis instructions, if the computed quantity exceeds the joint play threshold, to compare the rotational data and the translational data with rotational and translational thresholds for the rotational and translational joint testing, respectively, to identify the abnormality of the joint, and wherein a determination that the joint has an abnormality based on the computed quantity is a prerequisite to identifying the abnormality, such that a comparison of the rotational data and the translational data with the rotational and translational thresholds is implemented after the determination that the computed quantity exceeds the joint play threshold.

20. The system of claim 19, wherein the joint is a knee, and wherein the rotational motion comprises varus-valgus rotational movement of the knee.

21. The system of claim 20, wherein the rotational motion further comprises external-internal rotational movement of the knee.

* * * * *